US008394822B2

(12) United States Patent
Hutchings et al.

(10) Patent No.: US 8,394,822 B2
(45) Date of Patent: Mar. 12, 2013

(54) THIENO-PYRIDINE DERIVATIVES AS MEK INHIBITORS

(75) Inventors: Martin Clive Hutchings, Slough Berkshire (GB); Sarah Catherine Archibald, Slough Berskhire (GB); Daniel Christopher Brookings, Slough Berkshire (GB); Jeremy Martin Davis, Slough Berkshire (GB); James Andrew Johnson, Slough Berkshire (GB); Barry John Langham, Slough Berkshire (GB); Judi Charlotte Neuss, Slough Berkshire (GB)

(73) Assignee: UCB Pharma, S.A., Brussels (BE)

( * ) Notice: Subject to any disclaimer, the term of this patent is extended or adjusted under 35 U.S.C. 154(b) by 0 days.

(21) Appl. No.: 13/604,282

(22) Filed: Sep. 5, 2012

(65) Prior Publication Data

US 2012/0329774 A1 Dec. 27, 2012

Related U.S. Application Data

(60) Division of application No. 12/182,931, filed on Jul. 30, 2008, now Pat. No. 8,283,359, which is a continuation of application No. PCT/GB2007/000310, filed on Jan. 30, 2007.

(51) Int. Cl.
*A61K 31/44* (2006.01)
(52) U.S. Cl. ........................................ 514/301
(58) Field of Classification Search .................... 514/301
See application file for complete search history.

(56) References Cited

U.S. PATENT DOCUMENTS

| 6,579,882 B2 | 6/2003 | Stewart et al. |
| 2003/0220365 A1 | 11/2003 | Stewart |
| 2004/0138251 A1 | 7/2004 | Boschelli |
| 2005/0049276 A1 | 3/2005 | Kaufman |
| 2005/0227959 A1 | 10/2005 | Yoshida |
| 2007/0049603 A1 | 3/2007 | Miknis |
| 2009/0149437 A1 | 6/2009 | Hutchings |
| 2009/0264411 A1 | 10/2009 | Laing |
| 2010/0179124 A1 | 7/2010 | Johnson |
| 2011/0021558 A1 | 1/2011 | Brookings |
| 2011/0172191 A1 | 7/2011 | Johnson |

FOREIGN PATENT DOCUMENTS

| WO | WO 99/01421 | 1/1999 |
| WO | WO 00/41505 | 7/2000 |
| WO | WO 00/42022 | 7/2000 |
| WO | WO 02/06213 | 1/2002 |
| WO | WO 03/077855 | 9/2003 |
| WO | WO 03/077914 | 9/2003 |
| WO | WO 03/080625 | 10/2003 |
| WO | WO 2004/000846 | 12/2003 |
| WO | WO 2004/054505 | 7/2004 |
| WO | WO 2004/113347 | 12/2004 |
| WO | WO 2004/113348 | 12/2004 |
| WO | WO 2005/009975 | 2/2005 |
| WO | WO 2005/023251 | 3/2005 |
| WO | WO 2005/023759 | 3/2005 |
| WO | WO 2005/023818 | 3/2005 |
| WO | WO 2005/051300 | 6/2005 |
| WO | WO 2005/051301 | 6/2005 |
| WO | WO 2005/051302 | 6/2005 |
| WO | WO 2005/051906 | 6/2005 |
| WO | WO 2007/044515 | 4/2007 |
| WO | WO 2007/088345 | 8/2007 |
| WO | WO 2007/120101 | 10/2007 |
| WO | WO 2008/020206 | 2/2008 |
| WO | WO 2008/021389 | 2/2008 |
| WO | WO 2008/076415 | 6/2008 |

OTHER PUBLICATIONS

Bremner, D.H. et al.; "The Synthesis of Thienopyridines from ortho-Halogenated Pyridine Derivatives; Part 2" Synthesis; 1997, pp. 949.
Bremner, D.H. et al.; "The Synthesis of Thienopyridines from ortho-Halogenated Pyridine Derivatives; Part 3;" Sythesis; 1998; vol. 8; pp. 1095-1097.
Byrn et al.; "Solid-State Chemistry of Drugs;" $2^{nd}$ Ed.; SSCI, Inc.; West Lafayette, IN; Ch. 11; 1991; pp. 233-247.
Erian, Ayman Wahba et al; "An Easy Direct Conversion of Pyridine- and Pyrimidine-Thiones into Multi-Fused Heterocyclic Compounds;" Bulletin of the Chemical Society of Japan; 1998; pp. 2387-2391; 71(10).
West, Anthon R.; "Solid State Chemistry and its Applications;" Wiley, New York; 1988, pp. 358 & 365.
Wermuth, Camille G.; "Molecular Variation Based on Isosteric Replacements" in Chapter 13; The Practice of Medicinal Chemistry; Academic: 1996; pp. 203-237.
Hamdouchi et. al.; "Structure-based design of a new class of highly selective aminoimidazo [1, 2-a]pyridine-based inhibitors of cyclin dependent kinases;" Bioorganic & Medical Chemistry; Letters 15; 2005; pp. 1943-1947.
Written Opinion of the International Searching Authority published Jul. 31, 2008 for PCT/GB2007/000310 filed Jan. 30, 2007 (0002U).
Written Opinion of the International Searching Authority published Feb. 15, 2009 for PCT/GB2007/003114 filed Aug. 15, 2007 (0003U).
Written Opinion of the International Searching Authority published Jan. 23, 2010 for PCT/GB2008/002430 filed Jul. 16, 2008 (0004U).
Written Opinion of the International Searching Authority published Jul. 21, 2010 for PCT/GB2009/000144 filed Jan. 20, 2009 (0005U).
Written Opinion of the International Searching Authority published Dec. 19, 2010 for PCT/GB2009/001504 filed Jun. 12, 2009 (0006U).
International Search Report published Aug. 9, 2007 for PCT/GB2007/000310 filed Jan. 30, 2007 (0002U).
International Search Report published Apr. 24, 2008 for PCT/GB2007/003114 filed Aug. 15, 2007 (0003U).
International Search Report published Jan. 29, 2009 for PCT/GB2008/002430 filed Jul. 16, 2008 (0004U).
International Search Report published Jul. 30, 2009 for PCT/GB2009/000144 filed Jan. 20, 2009 (0005U).
International Search Report published Dec. 23, 2009 for PCT/GB2009/001504 filed Jun. 12, 2009 (0006U).

(Continued)

*Primary Examiner* — Rebecca Anderson
(74) *Attorney, Agent, or Firm* — Feldman Gale P.A.; Walter C. Frank

(57) ABSTRACT

A series of thieno[2,3-b]pyridine derivatives which are substituted in the 2-position by a substituted anilino moiety, being selective inhibitors of human MEK (MAPKK) enzymes, are accordingly of benefit in medicine, for example in the treatment of inflammatory, autoimmune, cardiovascular, proliferative (including oncological) and nociceptive conditions.

20 Claims, No Drawings

OTHER PUBLICATIONS

International Preliminary Report on Patentability published Aug. 5, 2008 for PCT/GB2007/000310 filed Jan. 30, 2007 (0002U).
International Preliminary Report on Patentability published Feb. 17, 2009 for PCT/GB2007/003114 filed Aug. 15, 2007 (0003U).
International Preliminary Report on Patentability published Jan. 26, 2010 PCT/GB2008/002430 filed Jul. 16, 2008 (0004U).
International Preliminary Report on Patentability published Jul. 27, 2010 for PCT/GB2009/000144 filed Jan. 20, 2009 (0005U).
International Preliminary Report on Patentability published Dec. 21, 2010 for PCT/GB2009/001504 filed Jun. 12, 2009 (0006U).
Klemm L. H. et al.; "Chemistry of Thienopyridines. XVII. Direct Halogenation of Thieno [2,3-b] pyridine (1);" *Journal of Heterocyclic Chemistry*; 1974; pp. 205-209.

THIENO-PYRIDINE DERIVATIVES AS MEK INHIBITORS

CROSS-REFERENCE TO RELATED APPLICATION

The present application is a divisional of U.S. patent application Ser. No. 12/182,931, filed Jul. 30, 2008, now U.S. Pat. No. 8,283,359, which is a continuation of International Application No.: PCT/GB2007/000310, filed Jan. 30, 2007, which claims priority under 119(a-d) to Great Britain Application No. GB 0601962.4, filed Jan. 31, 2006. Each of these applications is hereby incorporated herein by reference in its entirety.

The present invention relates to a class of thieno-pyridine derivatives and to their use in therapy. More particularly, the invention is concerned with thieno[2,3-b]pyridine derivatives which are substituted in the 2-position by a substituted anilino moiety. These compounds are selective inhibitors of MEK (MAPKK) enzymes, and are accordingly of benefit as pharmaceutical agents, especially in the treatment of adverse inflammatory, autoimmune, cardiovascular, proliferative (including oncological) and nociceptive conditions.

MEK enzymes are implicated in a variety of physiological and pathological functions that are believed to be operative in a range of human diseases. These functions are summarised in paragraphs [0004] and [0005] of US 2005/0049276 A1.

The compounds of use in the present invention, being potent and selective MEK inhibitors, are therefore beneficial in the treatment and/or prevention of various human ailments. These include autoimmune and inflammatory disorders such as rheumatoid arthritis, osteoarthritis, multiple sclerosis, asthma, inflammatory bowel disease, psoriasis and transplant rejection; cardiovascular disorders including thrombosis, cardiac hypertrophy, hypertension, and irregular contractility of the heart (e.g. during heart failure); proliferative disorders such as restenosis, and oncological conditions including leukaemia, glioblastoma, lymphoma, melanoma, and human cancers of the liver, bone, skin, brain, pancreas, lung, breast, stomach, colon, rectum, prostate, ovary and cervix; and pain and nociceptive disorders, including chronic pain and neuropathic pain.

In addition, the compounds of use in the present invention may be beneficial as pharmacological standards for use in the development of new biological tests and in the search for new pharmacological agents. Thus, the compounds of use in this invention may be useful as radioligands in assays for detecting compounds capable of binding to human MEK enzymes.

MEK inhibitors based on a fused bicyclic aromatic ring system attached to a substituted anilino moiety are known from the art. Examples of relevant publications include WO 2005/051906, WO 2005/023251, US-A-2005/0049276, WO 2005/009975, WO 03/077914 and WO 03/077855.

WO 2005/023818 describes a broad-ranging class of compounds based on a fused bicyclic aromatic ring system, which generically encompasses thieno-pyridine derivatives attached to a substituted anilino moiety but nowhere specifically discloses any precise compound of this type. No discrete pharmacological activity, in terms of an identifiable pharmacological mechanism, is ascribed to the compounds described therein, but they are nevertheless stated to be useful inter alia in the treatment of cell proliferative diseases such as cancer. US-A-2003/0220365 is also of relevance in a related context.

Nowhere in the prior art, however, is there the precise disclosure of a class of thieno[2,3-b]pyridine derivatives attached at the 2-position to a substituted anilino moiety. It has now been found that such compounds are particularly valuable as selective inhibitors of MEK enzymes.

The compounds of the present invention are potent and selective MEK inhibitors having a binding affinity ($IC_{50}$) for the human MEK1 and/or MEK2 enzyme of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound). The compounds of the invention may possess at least a 10-fold selective affinity, typically at least a 20-fold selective affinity, suitably at least a 50-fold selective affinity, and ideally at least a 100-fold selective affinity, for the human MEK1 and/or MEK2 enzyme relative to other human kinases.

The present invention provides a compound of formula (I), or a pharmaceutically acceptable salt, solvate or N-oxide thereof:

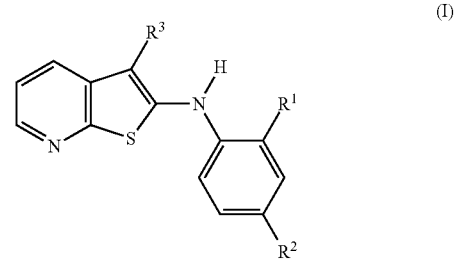

(I)

wherein
$R^1$ represents hydrogen, halogen or $C_{1-6}$ alkyl;
$R^2$ represents halogen or $C_{1-6}$ alkyl;
$R^3$ represents hydrogen, cyano, —$CO_2R^a$, —$CONR^bR^c$ or —$CON(OR^b)R^c$;
$R^a$ represents $C_{1-6}$ alkyl;
$R^b$ represents hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; and
$R^c$ represents hydrogen or $C_{1-6}$ alkyl (optionally substituted by hydroxy); or
$R^b$ and $R^c$, when taken together with the nitrogen atom to which they are both attached, represent azetidinyl, pyrrolidinyl, piperidinyl, morpholinyl, thiomorpholinyl, piperazinyl, homopiperidinyl, homomorpholinyl or homopiperazinyl, any of which groups may be optionally substituted by one or more substituents.

The present invention also provides a compound of formula (I) as depicted above, or a pharmaceutically acceptable salt, solvate or N-oxide thereof, wherein
$R^1$ and $R^2$ are as defined above;
$R^3$ represents cyano, —$CO_2R^a$, —$CONR^bR^c$ or —$CON(OR^b)R^c$;
$R^a$ represents $C_{1-6}$ alkyl;
$R^b$ represents hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; and
$R^c$ represents hydrogen or $C_{1-6}$ alkyl; or
$R^b$ and $R^c$, when taken together with the nitrogen atom to which they are both attached, represent azetidinyl, pyrrolidinyl, piperidinyl, morpholinyl, thiomorpholinyl, piperazinyl, homopiperidinyl or homomorpholinyl, any of which groups may be optionally substituted by one or more substituents.

For use in medicine, the salts of the compounds of formula (I) will be pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example, be formed by mixing a solution of the compound of the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

Suitable alkyl groups which may be present on the compounds of the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, iso-propyl, n-butyl, sec-butyl, isobutyl, tert-butyl and 2,2-dimethylpropyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

Specific $C_{3-7}$ cycloalkyl groups are cyclopropyl, cyclobutyl, cyclopentyl, cyclohexyl and cycloheptyl.

Suitable aryl groups include phenyl and naphthyl, preferably phenyl.

Suitable aryl($C_{1-6}$)alkyl groups include benzyl, phenylethyl, phenylpropyl and naphthylmethyl.

Suitable heterocycloalkyl groups, which may comprise benzo-fused analogues thereof, include azetidinyl, tetrahydrofuranyl, dioxolanyl, pyrrolidinyl, indolinyl, imidazolidinyl, tetrahydropyranyl, piperidinyl, 1,2,3,4-tetrahydroquinolinyl, 1,2,3,4-tetrahydroisoquinolinyl, piperazinyl, morpholinyl and thiomorpholinyl.

Suitable heteroaryl groups include furyl, benzofuryl, dibenzofuryl, thienyl, benzothienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl, pyridinyl, quinolinyl, isoquinolinyl, pyridazinyl, pyrimidinyl and pyrazinyl groups.

The term "halogen" as used herein is intended to include fluorine, chlorine, bromine and iodine atoms.

Where the compounds of formula (I) have one or more asymmetric centres, they may accordingly exist as enantiomers. Where the compounds of the invention possess two or more asymmetric centres, they may additionally exist as diastereomers. The invention is to be understood to extend to all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C=O$)-enol ($CH=CHOH$) tautomers. Formula (I) and the formulae depicted hereinafter are intended to represent all individual tautomers and all possible mixtures thereof, unless stated or shown otherwise.

In one embodiment, $R^1$ represents hydrogen. In another embodiment, $R^1$ represents halogen, particularly fluoro or chloro, especially fluoro. In a further embodiment, $R^1$ represents $C_{1-6}$ alkyl, especially methyl.

Typically, $R^1$ is fluoro.

In one embodiment, $R^2$ represents halogen, especially bromo or iodo. In another embodiment, $R^2$ represents $C_{1-6}$ alkyl, especially methyl.

In one specific embodiment, $R^2$ bromo. In another specific embodiment, $R^2$ is iodo.

Suitably, $R^a$ represents methyl or ethyl, especially ethyl.

Favourably, $R^b$ represents hydrogen; or $C_{1-6}$ alkyl, $C_{3-7}$ cycloalkyl($C_{1-6}$)alkyl, $C_{3-7}$ heterocycloalkyl or $C_{3-7}$ heterocycloalkyl($C_{1-6}$)alkyl, any of which groups may be optionally substituted by one or more substituents.

Suitably, $R^b$ represents hydrogen; or $C_{1-6}$ alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents.

Suitably, the group $R^b$, or the cyclic moiety —$NR^bR^c$, may be unsubstituted, or substituted by one or more substituents, typically by one or two substituents. In one embodiment, the group $R^b$, or the cyclic moiety —$NR^bR^c$, is unsubstituted. In another embodiment, the group $R^b$, or the cyclic moiety —$NR^bR^c$, is monosubstituted. In a further embodiment, the group $R^b$, or the cyclic moiety —$NR^bR^c$, is disubstituted.

Examples of typical substituents on $R^b$, or on the cyclic moiety —$NR^bR^c$, include $C_{1-6}$ alkyl, $C_{1-6}$ alkoxy, hydroxy, hydroxy($C_{1-6}$)alkyl, amino($C_{1-6}$)alkyl, (amino)(hydroxy)-($C_{1-6}$)alkyl, halogen, oxo, $C_{2-6}$ alkylcarbonyl, carboxy, $C_{2-6}$ alkoxycarbonyl, di($C_{1-6}$)alkylhydrazinylcarbonyl, amino, $C_{1-6}$ alkylamino, di($C_{1-6}$)alkylamino, $C_{2-6}$ alkylcarbonylamino, aminocarbonylamino, aminocarbonyl, $C_{1-6}$ alkylaminocarbonyl, di($C_{1-6}$)alkylaminocarbonyl, aminosulfonyl, $C_{1-6}$ alkylsulfonyl and $C_{1-6}$ alkylaminocarbonyl($C_{1-6}$)alkyl. Further examples include $C_{1-6}$ alkoxy($C_{1-6}$)alkyl, carboxy($C_{1-6}$)alkyl, $C_{2-6}$ alkoxycarbonyl($C_{1-6}$)alkyl, $C_{2-6}$ alkoxycarbonylamino and $C_{2-6}$ alkoxycarbonylamino($C_{1-6}$)alkyl.

Examples of particular substituents on $R^b$, or on the cyclic moiety —$NR^bR^c$, include methyl, methoxy, hydroxy, hydroxymethyl, 2-hydroxyethyl, aminomethyl, 2-amino-3-hydroxypropyl, fluoro, oxo, acetyl, carboxy, methoxycarbonyl, ethoxycarbonyl, tert-butoxycarbonyl, dimethylhydrazinylcarbonyl, amino, methylamino, 1,3-dimethyl-butylamino, dimethylamino, acetylamino, aminocarbonylamino, aminocarbonyl, ethylaminocarbonyl, diethylaminocarbonyl, aminosulfonyl, methylsulfonyl and methylaminocarbonylmethyl. Further examples include methoxymethyl, carboxymethyl, ethoxycarbonylmethyl, tert-butoxycarbonylamino and tert-butoxycarbonylaminomethyl.

Examples of favoured substituents on $R^b$, or on the cyclic moiety —$NR^bR^c$, include $C_{1-6}$ alkyl, $C_{1-6}$ alkoxy($C_{1-6}$)alkyl, hydroxy, hydroxy($C_{1-6}$)alkyl, amino, amino($C_{1-6}$)alkyl, carboxymethyl, $C_{2-6}$ alkoxycarbonyl, $C_{2-6}$ alkoxycarbonyl($C_{1-6}$)alkyl, di($C_{1-6}$)alkylamino, $C_{2-6}$ alkoxycarbonylamino and $C_{2-6}$ alkoxycarbonylamino($C_{1-6}$)alkyl.

Examples of specific substituents on $R^b$, or on the cyclic moiety —$NR^bR^c$, include methyl, methoxymethyl, hydroxy, hydroxymethyl, 2-hydroxyethyl, amino, aminomethyl, carboxymethyl, tert-butoxycarbonyl, ethoxycarbonylmethyl, dimethylamino, tert-butoxycarbonylamino and tert-butoxycarbonylaminomethyl.

Favoured values of $R^b$ include hydrogen, methyl, ethyl, propyl, cyclopropyl-methyl, azetidinyl, pyrrolidinyl, piperidinyl, azetidinylmethyl, dioxolanylmethyl, pyrrolidinylmethyl, morpholinylethyl and morpholinylpropyl, any of which groups may be optionally substituted by one or more substituents. Favoured substituents in this context include $C_{1-6}$ alkyl (especially methyl), hydroxy, amino, $C_{2-6}$ alkoxycarbonyl (especially tert-butoxycarbonyl) and di($C_{1-6}$)alkylamino (especially dimethylamino).

Specific values of $R^b$ include hydrogen, methyl, 2-hydroxyethyl, 3-hydroxypropyl, 1-hydroxyprop-2-yl, 2,3-dihydroxypropyl, 2-amino-2-methylpropyl, 2,2-dimethyl-3-(dimethylamino)propyl, cyclopropylmethyl, 1-tert-butoxycarbonylazetidin-3-yl, pyrrolidin-3-yl, 1-tert-butoxycarbonylpyrrolidin-3-yl, piperidin-3-yl, piperidin-4-yl, 1-methylpiperidin-4-yl, 1-tert-butoxycarbonylpiperidin-3-yl, 1-tert-butoxycarbonyl-piperidin-4-yl, 1-tert-butoxycarbonylazetidin-3-ylmethyl, 2,2-dimethyl-[1,3]dioxolan-4-ylmethyl, pyrrolidin-2-ylmethyl, 2-(morpholin-4-yl)ethyl and 3-(morpholin-4-yl)propyl.

Typically, $R^b$ represents hydrogen; or $C_{1-6}$ alkyl, optionally substituted by one or more, preferably one or two, hydroxy groups.

Typical values of $R^b$ include hydrogen, methyl, hydroxypropyl and dihydroxypropyl. In one embodiment, $R^b$ represents hydrogen. In another embodiment, $R^b$ represents methyl. In a further embodiment, $R^b$ represents hydroxypropyl, especially 3-hydroxypropyl. In an additional embodiment, $R^b$ represents dihydroxypropyl, especially 2,3-dihydroxypropyl.

In one embodiment, $R^c$ is hydrogen. In another embodiment, $R^c$ represents $C_{1-6}$ alkyl, especially methyl. In a further embodiment, $R^c$ represents hydroxy($C_{1-6}$)alkyl, e.g. hydroxyethyl (especially 2-hydroxyethyl).

Alternatively, the moiety $-NR^bR^c$ may suitably represent azetidin-1-yl, pyrrolidin-1-yl, piperidin-1-yl, morpholin-4-yl, thiomorpholin-4-yl, piperazin-1-yl, homopiperidin-1-yl or homomorpholin-4-yl, any of which groups may be optionally substituted by one or more substituents. The moiety $-NR^bR^c$ may also represent optionally substituted homopiperazin-1-yl.

Particular values for the cyclic moiety $-NR^bR^c$ include azetidin-1-yl, pyrrolidin-1-yl, piperidin-1-yl, morpholin-4-yl, piperazin-1-yl and homopiperazin-1-yl, any of which groups may be optionally substituted by one or more substituents.

Specific values of the cyclic moiety $-NR^bR^c$ include 3-hydroxyazetidin-1-yl, 3-aminoazetidin-1-yl, 3-(aminomethyl)azetidin-1-yl, 3-(tert-butoxycarbonylamino)azetidin-1-yl, 3-(tert-butoxycarbonylaminomethyl)azetidin-1-yl, pyrrolidin-1-yl, 2-(methoxy-methyl)pyrrolidin-1-yl, 3-hydroxypyrrolidin-1-yl, 3-aminopyrrolidin-1-yl, 3-(tert-butoxycarbonylamino)pyrrolidin-1-yl, 2-(hydroxymethyl)piperidin-1-yl, 4-amino-piperidin-1-yl, 4-(tert-butoxycarbonylamino)piperidin-1-yl, morpholin-4-yl, 2-(hydroxymethyl)morpholin-4-yl, piperazin-1-yl, 4-methylpiperazin-1-yl, 2-(hydroxymethyl)-piperazin-1-yl, 4-(2-hydroxyethyl)piperazin-1-yl, 4-(carboxymethyl)piperazin-1-yl, 4-(tert-butoxycarbonyl)-2-(hydroxymethyl)piperazin-1-yl, 4-(ethoxycarbonylmethyl)-piperazin-1-yl and homopiperazin-1-yl.

Suitably, the cyclic moiety $-NR^bR^c$ may be substituted by $C_{1-6}$ alkyl, especially methyl. Particular values of $-NR^bR^c$ include pyrrolidin-1-yl, morpholin-4-yl and 4-methylpiperazin-1-yl.

Typically, $R^3$ represents cyano, $-CO_2R^a$, $-CONR^bR^c$, or $-CON(OR^b)R^c$, in which $R^a$, $R^b$ and $R^c$ are as defined above. Suitably, $R^3$ represents cyano, $-CO_2R^a$ or $-CONR^bR^c$, especially cyano or $-CONR^bR^c$, in which $R^a$, $R^b$ and $R^c$ are as defined above. Suitably, $R^3$ represents $-CON(OR^b)R^c$, in which $R^b$ and $R^c$ are as defined above.

In one embodiment, $R^3$ represents cyano. In another embodiment, $R^3$ represents $-CO_2R^a$, in which $R^a$ is as defined above. In a further embodiment, $R^3$ represents $-CONR^bR^c$, in which $R^b$ and $R^c$ are as defined above. In an additional embodiment, $R^3$ represents $-CON(OR^b)R^c$, in which $R^b$ and $R^c$ are as defined above. In a still further embodiment, $R^3$ represents hydrogen.

A particular sub-group of compounds according to the invention is represented by the compounds of formula (II), and pharmaceutically acceptable salts, solvates and N-oxides thereof:

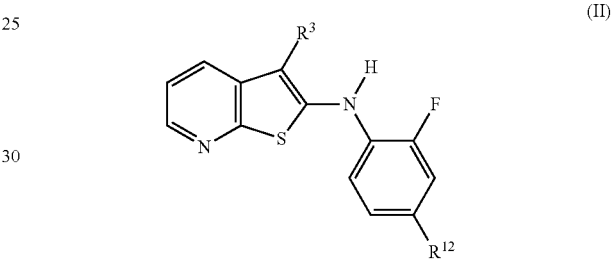

(II)

wherein
$R^{12}$ represents halogen; and
$R^3$ is as defined above.

In one specific embodiment, $R^{12}$ is bromo. In another specific embodiment, $R^{12}$ is iodo.

Specific novel compounds in accordance with the present invention include each of the compounds whose preparation is described in the accompanying Examples, and pharmaceutically acceptable salts and solvates thereof.

The present invention also provides a pharmaceutical composition which comprises a compound of formula (I) as defined above, or a pharmaceutically acceptable salt, solvate or N-oxide thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds according to the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds according to the present invention may be conveniently formulated as microionized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds according to the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of formula (I) above, and the N-oxides thereof, may be prepared by a process which comprises reacting a compound of formula (III), or an N-oxide thereof, with a compound of formula (IV):

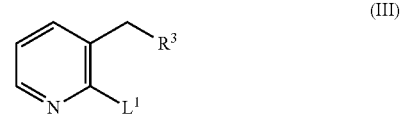

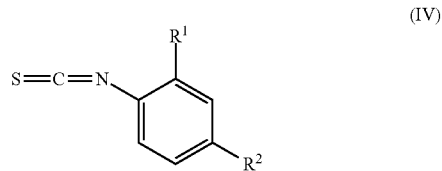

wherein $R^1$, $R^2$ and $R^3$ are as defined above, and $L^1$ represents a suitable leaving group.

The leaving group $L^1$ is typically a halogen atom, e.g. chloro.

The reaction is conveniently effected, at an elevated temperature if necessary, in a suitable solvent, e.g. dimethylsulphoxide, typically under basic conditions, e.g. in the presence of an inorganic base such as sodium hydride.

The intermediates of formula (IV) above may be prepared by reacting a compound of formula (V):

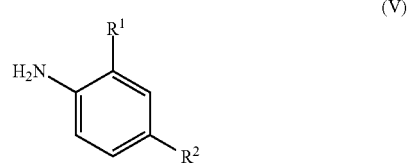

wherein $R^1$ and $R^2$ are as defined above; with thiophosgene.

The reaction is conveniently effected in a suitable solvent, typically a mixture of chloroform and water.

In another procedure, the compounds of formula (I) above wherein $R^3$ represents —$CONR^bR^c$ or —$CON(OR^b)R^c$, and the N-oxides thereof, may be prepared by a process which comprises reacting a compound of formula H—$NR^bR^c$ or H—$N(OR^b)R^c$ with a compound of formula (VI), or an N-oxide thereof:

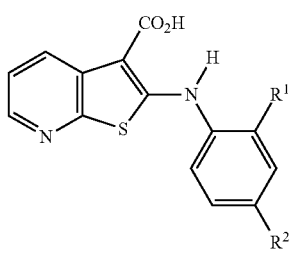

(VI)

wherein $R^1$, $R^2$, $R^b$ and $R^c$ are as defined above; in the presence of a condensing agent.

A suitable condensing agent is 1-(3-dimethylaminopropyl)-3-carbodiimide hydrochloride (EDC), in which case the reaction is conveniently effected in the presence of 1-hydroxybenzotriazole (HOBT) and N-methylmorpholine (NMM).

The compounds of formula (VI) above may be prepared by reacting the compound of formula (VII):

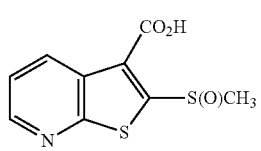

(VII)

with a compound of formula (V) as defined above.

The reaction may conveniently be effected by treating compound (V) with a base, e.g. lithium bis(trimethylsilyl)amide, in a suitable solvent, e.g. tetrahydrofuran, followed by the addition of compound (VII).

The intermediate of formula (VII) above may be prepared from a compound of formula (VIII):

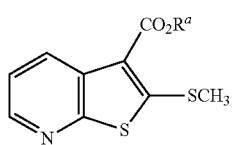

(VIII)

wherein $R^a$ is as defined above; by saponification of the ester moiety followed by oxidation of the methylsulfanyl group.

Saponification of the ester moiety —$CO_2R^a$ in compound (VIII) may be effected by treatment with an alkaline base, e.g. sodium hydroxide, in a suitable solvent, e.g. an aqueous mixture of a lower alkanol such as methanol and a cyclic ether such as tetrahydrofuran. Oxidation of the methylsulfanyl group in the resulting compound may then be effected by treatment with a suitable oxidising agent, e.g. Oxone® (potassium peroxymonosulfate), in an appropriate solvent, e.g. aqueous methanol.

The intermediates of formula (VIII) above may be prepared by reacting a compound of formula (III), wherein $R^3$ is —$CO_2R^a$ as defined above, with carbon disulfide, followed by treatment with a methyl halide such as iodomethane.

The reaction is conveniently effected in a suitable solvent, e.g. dimethylsulfoxide, in the presence of a base such as sodium hydride.

Where they are not commercially available, the starting materials of formula (III) and (V) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound of formula (I) wherein $R^3$ represents —$CO_2R^a$ may be converted into the corresponding compound wherein $R^3$ represents —$CONH_2$ by treatment with ammonia, typically in a lower alkanol solvent, e.g. ethanol, at elevated temperature and pressure. Alternatively, a compound of formula (I) wherein $R^3$ represents —$CO_2R^a$ may be converted into the corresponding compound wherein $R^3$ represents —$CONR^bR^c$ by treatment with the appropriate amine of formula H—$NR^bR^c$ in the presence of trimethylaluminium. A compound of formula (I) wherein $R^3$ represents —$CO_2R^a$ may be converted into the corresponding compound wherein $R^3$ represents hydrogen by treatment with an alkaline reagent such as lithium hydroxide under forcing conditions, e.g. by heating at reflux in a mixture of ethanol and water. A compound of formula (I) wherein $R^3$ contains a 2,2-dimethyl-[1,3]-dioxolan-4-ylmethyl moiety may be converted into the corresponding compound wherein $R^3$ contains a 2,3-dihydroxypropyl moiety by treatment with a mineral acid such as hydrochloric acid. A compound of formula (I) wherein $R^3$ contains a nitrogen atom to which a tert-butoxycarbonyl (BOC) group is attached may be converted into the corresponding compound wherein $R^3$ contains an N—H functionality by treatment with an acid, e.g. a mineral acid such as hydrochloric acid, or an organic acid such as trifluoroacetic acid. A compound of formula (I) wherein $R^3$ contains an N—H functionality may be converted into the corresponding compound wherein $R^3$ contains a nitrogen atom to which an ethoxycarbonylmethyl group is attached by treatment with ethyl chloroacetate, typically in the presence of triethylamine; the resulting compound may then be converted into the corresponding compound wherein $R^3$ contains a nitrogen atom to which a carboxymethyl group is attached by treatment with an alkaline reagent such as sodium hydroxide, typically in an aqueous solution of a lower alkanol such as ethanol. The pyridine-N-oxide derivative of a compound of formula (I) may be converted into the corresponding compound of formula (I) by treatment with triphenyl phosphine and phosphorus trichloride.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

The following Examples illustrate the preparation of compounds according to the invention.

The compounds in accordance with this invention potently inhibit the activity of human MEK enzyme.

In Vitro MEK Assay

MEK1 activity was measured in a cascade assay initiated by active Raf, via activation of MEK, Erk2 and subsequent phosphorylation of fluorescein-labelled Erk-tide substrate in an assay based on fluorescence polarisation (IMAP). The assay was carried out in 20 mM Tris+5 mM $MgCl_2$+2 mM DL-dithiothreitol+0.01% Tween 20 pH 7.2, containing 1.5 nM unactive MEK, 100 nM unactive Erk and 200 nM Erk-tide (all concentrations are final concentrations). Compounds, or DMSO controls, were tested at a final concentration of 2% DMSO, and the assay initiated in the presence of 5 μM ATP by addition of 1.25 nM active Raf in assay buffer. After 20 min at r.t., stop solution was added followed by IMAP binding beads, the assay mixture was then incubated for 90 min at r.t. (with shaking) and then read on a Molecular Devices LJL HT reader.

When tested in the above assay, the compounds of the accompanying Examples were all found to inhibit human MEK enzyme with $IC_{50}$ values of 10 μM or better.

| EXAMPLES Abbreviations used | |
|---|---|
| EtOAc | ethyl acetate |
| DMSO | dimethylsulphoxide |
| THF | tetrahydrofuran |
| DCM | dichloromethane |
| ether | diethyl ether |
| $CDCl_3$ | deuterochloroform |
| MeOH | methanol |
| MeCN | acetonitrile |
| EtOH | ethanol |
| ES | electrospray |
| DMF | N,N-dimethylformamide |
| HOBT | 1-hydroxybenzotriazole |
| $SiO_2$ | silica |
| NMM | N-methylmorpholine |
| h | hour(s) |
| min | minute(s) |
| r.t. | room temperature |
| aq | aqueous |
| sat. | saturated |
| RT | retention time |
| BOC | tert-butoxycarbonyl |

| EXAMPLES Abbreviations used | |
|---|---|
| LiHMDS | lithium bis(trimethylsilyl)amide |
| MCPBA | 3-chloroperoxybenzoic acid |
| EDC | 1-(3-dimethylaminopropyl)-3-carbodiimide hydrochloride |

All NMR spectra were obtained either at 300 MHz or 400 MHz.

Compounds were named with the aid of ACD Labs Name (v. 7.0) supplied by Advanced Chemical Development, Toronto, Canada.

Standard LCMS Method

The LC-MS system used comprises a Waters Alliance 2795 HT quaternary HPLC, Waters 996 Photo Diode Array (PDA) detector and Waters ZQ 4000 single quadrupole mass spectrometer. The ZQ can acquire data simultaneously in positive and negative electrospray ionisation modes.

| ZQ Mass Spectrometer | | | |
|---|---|---|---|
| Capillary | 3.5 kV | Cone | 50 V |
| Extractor | 2 V | Source Temp | 80° C. |
| Desolvation Temp | 200° C. | Cone Gas | 150 L/h |
| Desolvation Gas | 250 L/h | Multiplier | 650 V |

Data were acquired in a full scan from 100 to 1000 m/z.
Scan duration 0.80 s
Interscan delay 0.20 s
HPLC Analytical reverse phase separation was carried out on a Gemini C18 from Phenomenex 50×4.6 mm with 5 μm silica.
Injection Volume 5 μL
UV data 240 to 400 nm
Sample Temperature 20° C.
Column Temperature 30° C.
Flow Rate 0.9 mL/min
Split to ZQ ~0.40 mL/min
Solvent A: 90% 10 mM $NH_4CO_2$ in water/0.1% formic acid/10% $CH_3CN$
Solvent B: 90% $CH_3CN$/0.1% formic acid/10% 10 mM $NH_4CO_2$ in water
Solvent C: 90% 10 mM $NH_4CO_2$ in water/0.1% ammonia/10% $CH_3CN$
Solvent D: 90% $CH_3CN$/10% 10 mM $NH_4CO_2$ in water/0.1% ammonia

| Gradient Program | | | | |
|---|---|---|---|---|
| Time (min) | A % | B % | Flow | Curve |
| For method 5_95_pH = 3 | | | | |
| 0.00 | 95.0 | 5.0 | 0.900 | 1 |
| 2.00 | 5.0 | 95.0 | 0.900 | 6 |
| 4.00 | 5.0 | 95.0 | 0.900 | 6 |
| 5.00 | 95.0 | 5.0 | 0.900 | 6 |
| For method 5_95_pH = 10 | | | | |
| 0.00 | 95.0 | 5.0 | 0.900 | 1 |
| 2.00 | 5.0 | 95.0 | 0.900 | 6 |
| 4.00 | 5.0 | 95.0 | 0.900 | 6 |
| 5.00 | 95.0 | 5.0 | 0.900 | 6 |

Preparative UV-HPLC

The LC system comprises a Waters 2525 quaternary pump, a Waters 996 Photo Diode Array (PDA) detector, a Waters 2700 sample manager, a Column Fluidics Organiser and a Waters Fraction Collector operating in reverse phase at one of two pH systems.

Low pH System (Approximately pH 3.2)

The reverse phase separation was carried out on a Luna C18 from Phenomenex 100×21.2 mm with 5 μm silica.

Injection Volume 500 μL
UV data 254 nm
Flow Rate 20 mL/min
Solvent A 90% water/10% $CH_3CN$/0.1% formic acid
Solvent B 90% $CH_3CN$/10% water/0.1% formic acid High pH System (Approximately pH 9.5)

The reverse phase separation was carried out on a Gemini C18 from Phenomenex 150×21.2 mm with 10 μm silica.

Injection Volume 500 μL
UV data 254 nm
Flow Rate 20 mL/min
Solvent C 90% 10 mM $NH_4HCO_2$ in water/0.1% Ammonia/10% $CH_3CN$
Solvent D 90% $CH_3CN$/10% 10 mM $NH_4HCO_2$ in water/0.1% Ammonia Typical gradient profiles are described below:

| Time | A% | B% | C% | D% | Flow | Curve |
|---|---|---|---|---|---|---|
| Gradient Program for Low pH Method | | | | | | |
| 0.00 | 95.0 | 5.0 | 0.0 | 0.0 | 20 | 1 |
| 9.00 | 5.0 | 95.0 | 0.0 | 0.0 | 20 | 6 |
| 11.00 | 5.0 | 95.0 | 0.0 | 0.0 | 20 | 6 |
| 11.50 | 95.0 | 5.0 | 0.0 | 0.0 | 20 | 6 |
| 12.00 | 95.0 | 5.0 | 0.0 | 0.0 | 20 | 6 |
| Gradient Program for High pH Method | | | | | | |
| 0.00 | 0.0 | 0.0 | 95.0 | 5.0 | 20 | 1 |
| 9.00 | 0.0 | 0.0 | 5.0 | 95.0 | 20 | 6 |
| 11.00 | 0.0 | 0.0 | 5.0 | 95.0 | 20 | 6 |
| 11.50 | 0.0 | 0.0 | 95.0 | 5.0 | 20 | 6 |
| 12.00 | 0.0 | 0.0 | 95.0 | 5.0 | 20 | 6 |

Intermediate 1

2-Fluoro-4-iodo-1-isothiocyanatobenzene

Thiophosgene (3.55 mL, 46.4 mmol) was added to a rapidly-stirred mixture of 2-fluoro-4-iodoaniline (10.0 g, 42.2 mmol) in $CHCl_3$ (200 mL) and water (100 mL). The mixture was stirred at r.t. for 16 h. The organic phase was dried ($Na_2SO_4$) and concentrated in vacuo to give the title compound as an off-white crystalline solid (11.8 g, quant.). $\delta_H$ (DMSO-$d_6$) 7.87 (1H, dd, J 1.8, 9.5 Hz), 7.63 (1H, ddd, J 1.0, 1.8, 8.4 Hz), 7.25 (1H, dd, J 8.2, 8.4 Hz).

Intermediate 2

Ethyl 2-[(4-bromo-2-fluorophenyl)amino]thieno[2,3-b]pyridine-3-carboxylate

Prepared from ethyl (2-chloropyridin-3-yl)acetate (D. H. Bremner et al., Synthesis, 1997, 949) (500 mg, 2.5 mmol) and 4-bromo-2-fluorophenyl isothiocyanate (580 mg, 2.5 mmol) by the method of Example 1. Title compound obtained as an off-white solid (390 mg, 40%). $\delta_H$ (DMSO-$d_6$) 10.37 (1H, br s), 8.25 (1H, dd, J 1.4, 8.1 Hz), 8.19 (1H, d, J=4.8 Hz), 7.69 (1H, dd, J 1.8, 10.2 Hz), 7.56-7.45 (2H, m), 7.32 (1H, dd, J 4.5, 8.1 Hz), 4.35 (2H, q, J=7.1 Hz), 1.37 (3H, t, J=7.1 Hz). LCMS (ES$^+$) RT 4.66 minutes, 395 (M($^{79}$Br)+H)$^+$.

Intermediate 3

3-(tert-Butyldimethylsilanyloxy)propylamine

To a solution of N-(3-hydroxypropyl)phthalimide (5.25 g, 24.36 mmol) in DMF (20 mL) was added imidazole (16.6 g, 240 mmol) and tert-butyldimethylsilyl chloride (19 g, 120 mmol). The reaction was stirred at room temperature for 18 hours before the volatiles were removed in vacuo and a portion of the crude product was subjected to column chromatography ($SiO_2$, 1:1 DCM/hexanes) to give 2-[3-(tert-butyldimethyl-silanyloxy)propyl]isoindole-1,3-dione as a clear oil (5 g). 2-[3-(tert-Butyldimethyl-silanyloxy)propyl]isoindole-1,3-dione (5 g, 26.4 mmol) was dissolved in ethanol (50 ml) and methyl hydrazine (2.94 ml, 55.4 mmol) added. The reaction was heated to 75° C. for 8 hours before concentration in vacuo. The crude residue was triturated with a mixture of diethyl ether (150 mL) and hexanes (50 mL) and the resultant solid removed by filtration. The solvents were removed in vacuo to give the title compound as a pale yellow oil (1.8 g, 61%). $\delta_H$ (DMSO-$d_6$) 4.58 (2H, br s), 3.63-3.58 (2H, m), 2.67-2.62 (2H, m), 1.60-1.55 (2H, m), 0.83 (9H, d, J=1.1 Hz), 0.00 (6H, d, J=1.2 Hz). LCMS (ES$^+$) RT 1.77 minutes, 190 (M+H)$^+$.

Intermediate 4

2-Methylsulfanylthieno[2,3-b]pyridine-3-carboxylic acid ethyl ester

To a solution of ethyl (2-chloropyridin-3-yl)acetate (D. H. Bremner et al., Synthesis, 1997, 949) (8.0 g, 40.0 mmol) and carbon disulfide (3.18 g, 42.0 mmol) in DMSO (100 mL) was added sodium hydride portionwise (2.4 g, 60.0 mmol). After 60 minutes stirring at room temperature the mixture was heated at 80° C. for 2 hours. After this time the reaction mixture was allowed to cool to room temperature and methyl iodide (7.6 g, 54.0 mmol) added. After 18 hours ice (50 mL) was added and a yellow precipitate formed which was isolated via filtration to give the title compound as a grey solid (7.95 g, 78%). $\delta_H$ (DMSO-$d_6$) 8.60 (1H, dd, J 1.6, 8.2 Hz), 8.46, (1H, dd, J 1.6, 4.6 Hz), 7.35 (1H, dd, J 4.6, 8.2 Hz), 4.48 (2H, q, J=7.1 Hz), 2.71, (3H, s), 1.49 (3H, t, J=7.1 Hz).

Intermediate 5

2-Methylsulfanylthieno[2,3-b]pyridine-3-carboxylic acid

A mixture of Intermediate 4 (12.5 g, 50.0 mmol) in THF (200 mL) and MeOH (50 mL) was treated with sodium hydroxide solution (10% solution in water, 50 mL) and stirred at room temperature for 18 h. After this time the reaction mixture was reduced in vacuo to one third of its volume. Water (50 mL) was then added before 10% HCl was added until a white precipitate formed. This was filtered to give the title compound as a crystalline white solid (10.6 g, 95%). $\delta_H$ (DMSO-$d_6$) 13.50-13.20 (1H br s), 8.55 (1H, dd, J 1.2, 8.2 Hz), 8.48 (1H, dd, J 1.3, 4.5 Hz), 7.49 (1H, dd, J 4.6, 8.2 Hz), 3.25 (3H, s).

Intermediate 6

2-Methanesulfinylthieno[2,3-b]pyridine-3-carboxylic acid

Oxone (14.5 g, 24.0 mmol) dissolved in water (25 mL) was added to a rapidly stirred mixture of Intermediate 5 (10.6 g, 47 mmol) in MeOH (250 mL). The mixture was stirred at room temperature for 4 h. The reaction mixture was separated between DCM (300 mL) and water (200 mL). The organic layer was dried ($Na_2SO_4$) and concentrated in vacuo to give the title compound as a white crystalline solid (10.0 g, 88%). $\delta_H$ (DMSO-$d_6$) 14.20-13.80 (1H, br s), 8.73 (1H, dd, J 1.7, 8.3 Hz), 8.69 (1H, J 1.7, 4.6 Hz), 7.61 (1H, dd, J 4.6, 8.3 Hz), 3.05 (3H, s).

Intermediate 7

2-[(2-Fluoro-4-iodophenyl)amino]thieno[2,3-b]pyridine-3-carboxylic acid

To a stirred solution of 2-fluoro-4-iodoaniline (6.0 g, 25 mmol) in THF (100 mL) at 0° C. (ice bath) was added LiHMDS (1.0 M solution in THF, 20.0 mL, 20.0 mmol) slowly. The mixture was allowed to stir at room temperature for 30 minutes before cooling to 0° C. and Intermediate 6 (2.0 g, 8.3 mmol) was added portionwise. The mixture was stirred at room temperature for 1 hour. After this time the reaction mixture was poured onto ice and when at ambient temperature citric acid was added until a precipitate formed. The mixture was filtered to give the title compound as a pale brown crystalline solid (2.9 g, 84%). $\delta_H$ (DMSO-$d_6$) 14.00-13.00 (1H, br s), 10.80 (1H, s), 8.36 (1H, dd, J 1.3, 8.1 Hz), 8.32 (1H, dd, J, 1.3, 4.8 Hz), 7.84 (1H, dd, J 1.8, 10.1 Hz), 7.69 (1H, d, J=8.3 Hz), 7.54 (1H, m), 7.42 (1H, dd, J 8.3, 4.8 Hz).

Intermediate 8

4-Iodo-1-isothiocyanato-2-methylbenzene

To a stifling solution of 4-iodo-2-methylaniline (1.0 g, 4.2 mmol) in DCM (50 mL) was added water (20 mL) followed by thiophosgene (490 mg, 4.2 mmol). The reaction mixture was stirred overnight before the layers were separated and the organic layer dried ($Na_2SO_4$) and evaporated in vacuo to give the desired product as a brown solid (1.05 g, 89%). $\delta_H$ (CDCl$_3$) 7.75 (1H, d, J=1.2 Hz), 7.62 (1H, dd, J 1.2, 8.3 Hz), 7.15 (1H, d, J=8.3 Hz), 2.20 (3H, s).

Intermediate 9

2-Chloro-4-iodo-1-isothiocyanatobenzene

To a stirred solution of 2-chloro-4-iodoaniline (1.0 g, 3.9 mmol) in DCM (50 mL) was added water (20 mL) followed by thiophosgene (476 mg, 4.1 mmol). The reaction mixture was stirred overnight before the layers were separated and the organic layer dried ($Na_2SO_4$) and evaporated in vacuo to give the desired product as a brown solid (1.0 g, 86%). $\delta_H$ (CDCl$_3$) 7.79 (1H, d, J=1.9 Hz), 7.58 (1H, dd, J 1.9, 8.4 Hz), 6.97 (1H, d, J=8.4 Hz).

Intermediate 10

(2R)-2-[({2-[(2-Fluoro-4-iodophenyl)amino]thieno[2,3-b]pyridine-3-carbonyl}amino)-methyl]pyrrolidine-1-carboxylic acid tert-butyl ester

1-(3-Dimethylaminopropyl)-3-carbodiimide hydrochloride (139 mg, 0.72 mmol) was added to a solution of Intermediate 7 (150 mg, 0.36 mmol), 1-hydroxybenzotriazole (98 mg, 0.72 mmol), N-methylmorpholine (0.11 mL, 0.99 mmol) and (R)-2-(aminomethyl)-1-BOC-pyrrolidine (144 mg, 0.72 mmol) in N,N-dimethylformamide (5 mL). The reaction mixture was stirred at r.t. for 20 h, then poured into EtOAc (25 mL). The organic solution was washed with sat. brine (3×25 mL), dried ($Na_2SO_4$), filtered and concentrated in vacuo to give a brown solid. The crude product was subjected to column chromatography ($SiO_2$, 4:1 hexanes/EtOAc) to give the title compound, which was evaporated from ether to give a hard foam (135 mg, 63%). $\delta_H$ (CDCl$_3$) 11.67 (1H, s), 8.35-8.33 (2H, m), 8.04 (1H, br s), 7.54-7.43 (3H, m), 7.32-7.30 (1H, m), 4.19 (1H, m), 3.82-3.78 (1H, m), 3.53-3.35 (3H, m), 2.18-1.86 (3H, m), 1.78 (1H, m), 1.45 (9H, s).

Intermediate 11

(2S)-2-[({2-[(2-Fluoro-4-iodophenyl)amino]thieno[2,3-b]pyridine-3-carbonyl}amino)-methyl]pyrrolidine-1-carboxylic acid tert-butyl ester

Prepared from Intermediate 7 (150 mg, 0.36 mmol), 1-hydroxybenzotriazole (98 mg, 0.72 mmol), N-methylmorpholine (0.11 mL, 0.99 mmol), 1-(3-dimethylamino-propyl)-3-carbodiimide hydrochloride (139 mg, 0.72 mmol) and (S)-2-(aminomethyl)-1-BOC-pyrrolidine (144 mg, 0.72 mmol) by the method of Intermediate 10. The title compound was evaporated from ether to give a colourless hard foam (139 mg, 64%). $\delta_H$ (CDCl$_3$) 11.67 (1H, s), 8.35-8.33 (2H, m), 8.04 (1H, br s), 7.54-7.43 (3H, m), 7.32-7.30 (1H, m), 4.19 (1H, m), 3.82-3.78 (1H, m), 3.53-3.35 (3H, m), 2.18-1.86 (3H, m), 1.78 (1H, m), 1.45 (9H, s).

Intermediate 12

(2-Chloropyridin-3-yl)acetic acid

2-Chloro-3-(cyanomethyl)pyridine (D. H. Bremner et al., *Synthesis*, 1997, 949) (10.3 g, 67.1 mmol) in conc. HCl (100 mL) was heated at reflux for 3 h. The reaction mixture was concentrated in vacuo and the residue suspended in water. The white solid was collected by filtration and washed with water, then dried in vacuo yielding the required product (11.15 g). $\delta_H$ (DMSO-$d_6$) 12.60 (1H, br s), 8.32 (1H, dd, J 4.7, 1.9 Hz), 7.86 (1H, dd, J 7.5, 1.9 Hz), 7.40 (1H, dd, J 7.5, 4.7 Hz), 3.75 (2H, s). LCMS (ES$^+$) RT 1.85 minutes, 174 (M+H)$^+$.

Intermediate 13

(2-Chloropyridin-3-yl)acetic acid methyl ester

To a suspension of Intermediate 12 (3.88 g, 22.6 mmol) in methanol was added acetyl chloride (1.8 mL, 24.9 mmol) and the mixture heated at 70° C. for 18 hours. The solvents were removed in vacuo to give the title compound as a pale brown oil (4.63 g, quant). $\delta_H$ (DMSO-$d_6$) 8.35 (1H, dd, J 4.7, 1.9 Hz), 7.88 (1H, dd, J 8.5, 1.9 Hz), 7.43 (1H, dd, J 8.5, 4.7 Hz), 3.80 (2H, s), 3.65 (3H, s). LCMS (ES$^+$) RT 2.40 minutes, 186 (M+H)$^+$.

Intermediate 14

2-[(2-Fluoro-4-iodophenyl)amino]thieno[2,3-b]pyridine-3-carboxylic acid methyl ester

To a solution of Intermediate 13 (4.1 g, 22.1 mmol) and Intermediate 1 (6.16 g, 22.1 mmol) in dry DMSO under nitrogen was added sodium hydride (1.05 g, 24.3 mmol, 60 wt % dispersion in mineral oil). The mixture was stirred at room temperature for 15 minutes then heated to 90° C. for 3 hours. The reaction was cooled, then poured onto iced water (200 mL). The aqueous phase was extracted with EtOAc (3×200 mL), the combined organics washed with brine, dried (MgSO$_4$), filtered and the solvents removed in vacuo. The sticky yellow solid was triturated with ethanol to give a fine yellow solid which was collected by filtration, washed with diethyl ether and dried under suction to give the title compound as a pale yellow solid (1.73 g). $\delta_H$ (DMSO-d$_6$) 10.30 (1H, s), 8.36-8.31 (2H, m), 7.87 (1H, dd, J 1.9, 10.0 Hz), 7.70 (1H, d, J=6.6 Hz), 7.51 (1H, t, J=8.5 Hz), 7.42 (1H, dd, J 5.7, 8.1 Hz), 3.94 (3H, s). LCMS (ES$^+$) RT 4.00 minutes, 429 (M+H)$^+$.

Intermediate 15

2-(2-Chloropyridin-3-yl)-N-methoxy-N-methylacetamide

Intermediate 12 (500 mg, 2.9 mmol) in dichloromethane (20 mL) with N,O-dimethylhydroxylamine (300 mg, 3.04 mmol), EDC (583 mg, 3.04 mmol) and N-methyl-morpholine (0.98 mL, 8.70 mmol) were stirred at r.t. for 18 h. The reaction mixture was washed with 2M HCl, and the organic phase was dried (magnesium sulphate) and concentrated in vacuo. Chromatography (SiO$_2$, 1:1 ethyl acetate:DCM) yielded the title compound (320 mg) as a white solid. $\delta_H$(DMSO-d$_6$) 8.31 (1H, dd, J 4.7, 1.9 Hz), 7.81 (1H, dd, J 7.5, 1.9 Hz), 7.40 (1H, dd, J 7.5, 4.7 Hz), 3.93 (2H, s), 3.76 (3H, s), 3.15 (3H, s). LCMS (ES$^+$) RT 2.22 minutes, 215/217 (M+H)$^+$.

Intermediate 16

2-(2-Chloro-1-oxypyridin-3-yl)-N-methoxy-N-methylacetamide

Intermediate 15 (270 mg, 1.25 mmol) was dissolved in DCM (5 mL) and treated with mCPBA (324 mg, 1.88 mmol). After stifling at r.t. for 3 days the reaction mixture was poured directly onto a flash column and chromatographed (SiO$_2$, ethyl acetate→5% methanol in ethyl acetate), yielding the required product (265 mg) as a white solid. $\delta_H$ (DMSO-d$_6$) 8.39 (1H, dd, J 5.4, 2.5 Hz), 7.37-7.35 (2H, m), 3.98 (2H, s), 3.76 (3H, s), 3.15 (3H, s). LCMS (ES$^+$) RT 1.81 minutes, 231/233 (M+H)$^+$.

EXAMPLE 1

Ethyl 2-[(2-fluoro-4-iodophenyl)amino]thieno[2,3-b]pyridine-3-carboxylate

Sodium hydride (650 mg of a 60% dispersion in mineral oil, 16.2 mmol) was added portionwise over 10 min to a mixture of Intermediate 1 (3.75 g, 13.5 mmol) and ethyl (2-chloropyridin-3-yl)acetate (D. H. Bremner et al., *Synthesis*, 1997, 949) (2.7 g, 13.5 mmol) in DMSO (25 mL). When gas evolution had slowed the mixture was heated at 70° C. for 3 h then left at r.t. overnight. Water (150 mL) was added and the liquid decanted off from the resulting solid. The solid mass was treated with ethanol (40 mL) to give a fine white suspension which was filtered off, washed with ethanol (10 mL) and ether (2×15 mL) and dried in vacuo at 40° C. to give the title compound as a white solid (2.90 g, 48%). $\delta_H$(DMSO-d$_6$) 10.40 (1H, s), 8.40-8.30 (2H, m), 7.85 (1H, dd, J 1.9, 10.1 Hz), 7.70 (1H, d, J=8.5 Hz), 7.55-7.49 (1H, m), 7.43 (1H, dd, J 4.9, 8.0 Hz), 4.43 (2H, q, J=7.9 Hz), 1.41 (3H, t, J=7.9 Hz). LCMS (ES$^+$) RT 5.27 minutes, 443 (M+H)$^+$.

EXAMPLE 2

2-[(2-Fluoro-4-iodophenyl)amino]-N-methylthieno[2,3-b]pyridine-3-carboxamide

Trimethylaluminium (1.5 mL of a 2M solution in hexane, 3.0 mmol) was added to a solution of methylamine (1.5 mL of a 2M solution in THF, 3.0 mmol) in toluene (5 mL). After 5 min Example 1 (250 mg, 0.60 mmol) was added and the mixture heated at 100° C. for 4 h. After cooling the reaction was quenched with sat. ammonium chloride solution (75 mL) and HCl (10 mL, 2M) then extracted with EtOAc (80 mL). The organic phase was dried (Na$_2$SO$_4$) and concentrated in vacuo to give a solid. Trituration with ether (30 mL) and filtration gave the title compound as an off-white solid (138 mg, 57%). $\delta_H$ (CDCl$_3$) 11.13 (1H, br s), 8.25 (1H, dd, J 1.4, 4.7 Hz), 7.80 (1H, dd, J 1.4, 8.2 Hz), 7.46-7.42 (2H, m), 7.33 (1H, dd, J 8.3, 8.3 Hz), 7.21 (1H, dd, J 4.7, 8.2 Hz), 5.82 (1H, br s), 3.00 (3H, d, J=4.8 Hz). LCMS (ES$^-$) RT 3.63 minutes, 426 (M−H)$^-$.

EXAMPLE 3

2-[(2-Fluoro-4-iodophenyl)amino]-N,N-dimethylthieno[2,3-b]pyridine-3-carboxamide Prepared from Example 1 (100 mg, 0.23 mmol) and dimethylamine (0.35 mL of 2.0M solution in THF, 0.7 mmol) by the method of Example 2. Title compound obtained as a white solid (21 mg, 20%). $\delta_H$(DMSO-d$_6$) 9.12 (1H, s), 8.35 (1H, dd, J 1.6, 4.7 Hz), 7.77 (1H, dd, J 1.6, 8.1 Hz), 7.67 (1H, dd, J 1.9, 10.6 Hz), 7.48 (1H, dd, J 1.1, 1.9 Hz), 7.35 (1H, dd, J 4.7, 8.0 Hz), 7.15-7.10 (1H, m), 2.87 (6H, s). LCMS (ES$^+$) RT 3.29 minutes, 442 (M+H)$^+$.

EXAMPLE 4

N-(2-Fluoro-4-iodophenyl)-3-(morpholin-4-ylcarbonyl)thieno[2,3-b]pyridin-2-amine Prepared from Example 1 (250 mg, 0.60 mmol) and morpholine (0.26 mL, 3 mmol) by the method of Example 2. Title compound obtained as a white solid (215 mg, 78%). $\delta_H$ (DMSO-d$_6$) 9.22 (1H, br s), 8.34 (1H, dd, J 1.4, 4.6 Hz), 7.81 (1H, dd, J 1.4, 8.0 Hz), 7.68 (1H, dd, J 1.9, 10.5 Hz), 7.50-7.46 (1H, m), 7.35 (1H, dd, J 4.6, 8.0 Hz), 7.13 (1H, dd, J 8.6, 8.6 Hz), 3.54-3.48 (4H, m), 3.43-3.39 (4H, m). LCMS (ES$^+$) RT 3.17 minutes, 484 (M+H)$^+$.

EXAMPLE 5

N-(2-Fluoro-4-iodophenyl)-3-[(4-methylpiperazin-1-yl)carbonyl]thieno[2,3-b]pyridin-2-amine Trimethylaluminium (1.5 mL of a 2M solution in hexane, 3.0 mmol) was added to a solution of 1-methylpiperazine (0.333 mL, 3.0 mmol) in toluene (5 mL). After 10 min Example 1 (250 mg, 0.60 mmol) and toluene (2 mL) were added and the mixture heated at 90° C. for 6 h. After cooling the mixture was quenched with NaOH (50 mL, 1M) and extracted with EtOAc (50 mL plus 25 mL). The combined organic extracts were washed with sat. brine (50 mL), dried (Na$_2$SO$_4$) and concentrated in vacuo to give a yellow solid. Trituration with hexane/ether (10:1, mL) and filtration gave the title compound as a pale yellow solid (245 mg, 87%). $\delta_H$ (DMSO-$d_6$) 9.13 (1H, br s), 8.37 (1H, br d, J=4.4 Hz), 7.79 (1H, br d, J=7.8 Hz), 7.67 (1H, br d, J=10.4 Hz), 7.47 (1H, br d, J=8.4 Hz), 7.37 (1H, dd, J 4.7, 8.1 Hz), 7.10 (1H, m), 3.30 (4H, br s), 2.21 (4H, br s), 2.14 (3H, s). LCMS (ES$^+$) RT 2.09 minutes, 497 (M+H)$^+$.

EXAMPLE 6

2-[(4-Bromo-2-fluorophenyl)amino]-N-(2,3-dihydroxypropyl)thieno[2,3-b]pyridine-3-carboxamide Trimethylaluminium (0.95 mL of a 2M solution in hexane, 1.90 mmol) was added to a solution of 2,2-dimethyl-1,3-dioxolane-4-methanamine (249 mg, 1.9 mmol) in toluene (4 mL). After 2 minutes Intermediate 2 (150 mg, 0.38 mmol) was added and the mixture heated at 90° C. for 4 h. After cooling the reaction was quenched with sat. ammonium chloride solution (5 mL) and HCl (5 mL, 2M), stirred, then extracted with EtOAc (2×25 mL) and DCM (25 mL). The organic phase was dried (Na$_2$SO$_4$) and concentrated in vacuo to give a solid. Trituration with ether/hexane (1:3, 10 mL) and filtration gave the title compound as a white solid (95 mg, 57%). $\delta_H$ (DMSO-$d_6$) 10.64 (1H, br s), 8.36 (1H, dd, J 1.4, 4.7 Hz), 8.20 (1H, dd, J 1.4, 8.2 Hz), 7.89 (1H, dd, J 8.8, 8.8 Hz), 7.69 (1H, dd, J 2.1, 10.6 Hz), 7.58 (1H, dd, J 8.8, 8.8 Hz), 7.48-7.41 (2H, m), 4.86 (1H, d, J=5.0 Hz), 4.64 (1H, t, J=5.7 Hz), 3.72-3.66 (1H, m), 3.52-3.36 (3H, m), 3.31-3.22 (1H, m). LCMS (ES$^+$) RT 2.80 minutes, 440 (M($^{79}$Br)+H)$^+$.

EXAMPLE 7

2-[(2-Fluoro-4-iodophenyl)amino]-N-(2,3-dihydroxypropyl)thieno[2,3-b]pyridine-3-carboxamide Prepared from Example 1 (150 mg, 0.34 mmol) and 2,2-dimethyl-1,3-dioxolane-4-methanamine (0.14 mL, 1.0 mmol) by the method of Example 6. Title compound obtained as a pale-yellow solid (94 mg, 57%). $\delta_H$ (DMSO-$d_6$) 10.68 (1H, s), 8.36-8.35 (1H, m), 8.20 (1H, dd, J 1.2, 8.2 Hz), 7.90-7.87 (1H, m), 7.76 (1H, dd, J 1.7, 10.4 Hz), 7.62-7.59 (1H, m), 7.45-7.40 (2H, m), 4.86 (1H, d, J=5.0 Hz), 4.64 (1H, t, J=5.7 Hz), 3.72-3.64 (1H, m), 3.51-3.41 (3H, m), 3.40-3.34 (1H, m). LCMS (ES$^+$) RT 2.91 minutes, 488 (M+H)$^+$.

EXAMPLE 8

Ethyl 2-[(2-fluoro-4-iodophenyl)amino]thieno[2,3-b]pyridine-3-carboxylate 7-oxide Prepared from Intermediate 1 (2.38 g, 8.58 mmol) and ethyl (2-chloro-1-oxidopyridin-3-yl)acetate (D. H. Bremner et al., Synthesis, 1997, 949) (1.85 g, 8.58 mmol) by the method of Example 1. Title compound obtained as a pale yellow solid (3.10 g, 79%). $\delta_H$ (DMSO-$d_6$) 10.31 (1H, br s), 8.20 (1H, d, J=5.9 Hz), 7.94 (1H, d, J 7.8 Hz), 7.89 (1H, dd, J 1.8, 10.0 Hz), 7.72 (1H, d, J=8.4 Hz), 7.55-7.46 (2H, m), 4.41 (2H, q, J=8.4 Hz), 1.40 (3H, t, J=7.1 Hz). LCMS (ES$^+$) RT 3.44 minutes, 459 (M+H)$^+$.

EXAMPLE 9

N-(2,3-Dihydroxypropyl)-2-[(2-fluoro-4-iodophenyl)amino]thieno[2,3-b]pyridine-3-carboxamide 7-oxide Prepared from Example 8 (200 mg, 0.43 mmol) and 2,2-dimethyl-1,3-dioxolane-4-methanamine (0.18 mL, 1.3 mmol) by the method of Example 6. Title compound obtained as a white solid (32 mg, 15%). $\delta_H$ (DMSO-$d_6$) 10.60 (1H, s), 8.22 (1H, m), 7.90 (1H, s), 7.84-7.76 (2H, m), 7.64-7.60 (1H, m), 7.45-7.40 (2H, m), 4.78 (1H, d, J=4.9 Hz), 4.64 (1H, t, J=5.6 Hz), 3.70-3.60 (1H, m), 3.50-3.15 (4H, m). LCMS (ES$^-$) RT 2.37 minutes, 502 (M−H)$^-$.

EXAMPLE 10

2-[(2-Fluoro-4-iodophenyl)amino]thieno[2,3-b]pyridine-3-carbonitrile

To a solution of (2-chloropyridin-3-yl)acetonitrile (D. H. Bremner et al., Synthesis, 1997, 949) (700 mg, 4.59 mmol) and Intermediate 1 (1.28 g, 4.60 mmol) in dry DMSO (15 mL) was added sodium hydride (202 mg, 60% in mineral oil, 5.06 mmol). The mixture was stirred at room temperature for 15 minutes before heating to 90° C. for four hours. The reaction mixture was poured into water (80 mL) and the solid precipitate filtered and washed with water/ethanol (2:1 mixture, 50 mL) followed by diethyl ether/hexane (1:1 mixture, 20 mL). The solid was dried in a vacuum oven and recrystallised from ethanol/water to give the title compound as a pale brown solid (800 mg, 45%). $\delta_H$ (DMSO-$d_6$) 10.40 (1H, s), 8.37 (1H, dd, J 1.3, 4.6 Hz), 7.83-7.81 (2H, m), 7.64 (1H, d, J=8.3 Hz), 7.44 (1H, dd, J 4.7, 8.0 Hz), 7.33 (1H, dd, J 8.3, 8.3 Hz). LCMS RT 3.08 minutes, (ES$^-$) 394 (M−H)$^-$, (ES$^+$) 396 (M+H)$^+$.

EXAMPLE 11

2-[(2-Fluoro-4-iodophenyl)amino]thieno[2,3-b]pyridine-3-carboxylic acid amide

A solution of Example 1 (250 mg, 0.56 mmol) in ethanol (5 mL) was added to liquid ammonia (15 mL) and the mixture heated in a Parr apparatus to 95° C. at 800 psi for 18 hours. The volatiles were removed in vacuo to give an oily brown residue. Repeated trituration with ethanol and DCM afforded the title compound as a white solid (18 mg). $\delta_H$ (DMSO-$d_6$) 11.20 (1H, bs), 8.34 (1H, d, J=3.4 Hz), 8.20 (1H, dd, J 8.2, 1.3 Hz), 7.76 (1H, dd, J 10.4, 1.8 Hz), 7.62 (1H, d, J=8.2 Hz), 7.57 (2H, br s), 7.49-7.39 (2H, m). LCMS (ES$^+$) RT 3.11 minutes, 412 (M+H)$^+$.

EXAMPLE 12

[2-[(2-Fluoro-4-iodophenyl)amino]thieno[2,3-b]pyridin-3-yl] (pyrrolidin-1-yl)methanone Prepared from Example 1 (250 mg, 0.60 mmol) and pyrrolidine (0.25 mL, 3 mmol) by the method of Example 2. Title compound obtained as a pale yellow solid (136 mg, 51%). $\delta_H$ (DMSO-$d_6$) 9.21 (1H, br s), 8.35 (1H, dd, J 1.6, 4.7 Hz), 7.81 (1H, dd, J 1.6, 8.1 Hz), 7.67 (1H, dd, J 1.9, 10.5 Hz), 7.50-7.46 (1H, m), 7.35 (1H, dd, J 4.7, 8.1 Hz), 7.13 (1H, dd, J 8.6, 8.6 Hz), 3.32-3.30 (4H, m), 1.78-1.73 (4H, m). LCMS (ES$^+$) RT 3.32 minutes, 468 (M+H)$^+$.

EXAMPLE 13

2-[(2-Fluoro-4-iodophenyl)amino]thieno[2,3-b]pyridine-3-carboxylic acid (3-hydroxy-propyl)amide Example 1 (500 mg, 1.13 mmol) was dissolved in dry toluene (6 mL) under nitrogen. To this solution was added trimethylaluminium (2.83 mL of a 2M solution in hexane, 5.66 mmol) over 5 minutes. After 10 minutes a solution of Intermediate 3 (1.07 g, 5.66 mmol) in dry toluene (5 mL) was added and the reaction heated to 100° C. for 6 hours. The reaction was allowed to cool to room temperature and treated with 2M HCl (10 mL) and water (30 mL). The mixture was extracted with ethyl acetate (3×50 mL), then the organic phases were dried over $Na_2SO_4$ and filtered and the solvents removed in vacuo. The crude residue was dissolved in methanol (30 mL), treated with 2M HCl (20 mL) and stirred at ambient temperature for 18 hours. The mixture was concentrated in vacuo, treated with 2M NaOH (20 mL) and extracted with ethyl acetate (3×50 mL). The organic phases were dried over $Na_2SO_4$, filtered, and the volatiles removed in vacuo. The residual solid was triturated with diethyl ether (10 mL) and dried in a vacuum oven to give the title compound as a pale yellow solid (100 mg, 19%). $\delta_H$ (DMSO-$d_6$) 10.75 (1H, br s), 8.35 (1H, m), 8.17 (1H, d, J=7.9 Hz), 8.01 (1H, br s), 7.75 (1H, d, J=10.1 Hz), 7.59 (1H, d, J=8.1 Hz), 7.44-7.41 (2H, m), 4.55 (1H, t, J=5.1 Hz), 3.54-3.48 (2H, m), 3.41-3.34 (2H, m), 1.75-1.67 (2H, m). LCMS (ES$^+$) RT 3.22 minutes, 472 (M+H)$^+$.

EXAMPLE 14

2-[(2-Fluoro-4-iodophenyl)amino]thieno[2,3-b]pyridine-3-carboxylic acid (2(S),3-dihydroxypropyl) amide Prepared from Example 1 (1.0 g, 2.26 mmol) and (S)-(2,2-dimethyl-1,3-dioxolan-4-yl)methylamine (1.48 g, 11.3 mmol) by the method of Example 6. Title compound obtained as a white solid (425 mg, 39%). $\delta_H$ (DMSO-$d_6$) 10.67 (1H, bs), 8.36 (1H, d, J=3.8 Hz), 8.20 (1H, d, J=8.5 Hz), 7.88 (1H, bs), 7.76 (1H, d, J=10.5 Hz), 7.61 (1H, d, J=8.5 Hz), 7.46-7.40 (2H, m), 4.86 (1H, d, J=5.0 Hz), 4.64 (1H, t, J=5.7 Hz), 3.72-3.67 (1H, m), 3.52-3.38 (3H, m), 3.30-3.22 (1H, m). LCMS (ES$^+$) RT 2.91 minutes, 488 (M+H)$^+$.

EXAMPLE 15

2-[(2-Fluoro-4-iodophenyl)amino]thieno[2,3-b]pyridine-3-carboxylic acid (2(R),3-dihydroxypropyl) amide Prepared from Example 1 (500 mg, 1.13 mmol) and (R)-(2,2-dimethyl-1,3-dioxolan-4-yl)methylamine (655 g, 4.52 mmol) by the method of Example 6. Title compound obtained as a white solid (100 mg, 18%). $\delta_H$ (DMSO-$d_6$) 10.67 (1H, bs), 8.36 (1H, d, J=3.8 Hz), 8.20 (1H, d, J=8.5 Hz), 7.88 (1H, bs), 7.76 (1H, d, J=10.5 Hz), 7.61 (1H, d, J=8.5 Hz), 7.46-7.40 (2H, m), 4.86 (1H, d, J=5.0 Hz), 4.64 (1H, t, J=5.7 Hz), 3.72-3.67 (1H, m), 3.52-3.38 (3H, m), 3.30-3.22 (1H, m). LCMS (ES$^+$) RT 2.91 minutes, 488 (M+H)$^+$.

EXAMPLE 16

2-[(4-Bromo-2-fluorophenyl)amino]thieno[2,3-b]pyridine-3-carboxylic acid methylamide Prepared from Intermediate 2 (150 mg, 0.38 mmol) and a 2M solution of methylamine in THF (0.95 mL, 1.9 mmol) by the method of Example 2. Title compound obtained as a white solid (125 mg, 87%). $\delta_H$ (DMSO-$d_6$) 10.83 (1H, bs), 8.35 (1H, dd, J 1.4, 4.6 Hz), 8.18 (1H, dd, J 1.4, 8.2 Hz), 7.92 (1H, bs), 7.69 (1H, dd, J 2.1, 10.6 Hz), 7.59 (1H, dd, J 8.8, 8.8 Hz), 7.48-7.43 (1H, m), 7.42 (1H, dd, J 8.2, 4.6 Hz), 2.83 (3H, d, J=4.5 Hz). LCMS (ES$^+$) RT 3.45 minutes, 380/382 [Br$^{79}$/Br$^{81}$] (M+H)$^+$.

EXAMPLE 17

2-[(4-Iodophenyl)amino]thieno[2,3-b]pyridine-3-carboxylic acid ethyl ester

Prepared from ethyl (2-chloropyridin-3-yl)acetate (D. H. Bremner et al., *Synthesis*, 1997, 949) (750 mg, 3.8 mmol) and 4-iodophenyl isothiocyanate (1.0 g, 3.8 mmol) by the method of Example 1. Title compound obtained as an off-white solid (800 mg, 50%). $\delta_H$ (DMSO-$d_6$) 10.34 (1H, br s), 8.33-8.30 (2H, m), 7.79 (2H, dt, J 2.0, 6.7 Hz), 7.43-7.31 (3H, m), 4.40 (2H, q, J=7.1 Hz), 1.40 (3H, t, J=7.1 Hz). LCMS (ES$^+$) RT 4.31 minutes, 425 (M+H)$^+$.

EXAMPLE 18

2-[(4-Iodo-2-methylphenyl)amino]thieno[2,3-b]pyridine-3-carbonitrile

To a stirred solution of Intermediate 8 (429 mg, 3.28 mmol) and (2-chloropyridin-3-yl)acetonitrile (D. H. Bremner et al., *Synthesis*, 1997, 949) (500 mg, 3.28 mmol) in DMSO (20 mL) was added sodium hydride (164 mg, 4.1 mmol). When evolution of gases had finished the reaction mixture was heated for 3 hours at 80° C. After this time the reaction mixture was poured onto ice and extracted into DCM (2×50 mL). The organics were dried (Na$_2$SO$_4$) and then evaporated in vacuo to give a brown residue. Column chromatography (SiO$_2$, 5:1 hexane:EtOAc) gave the title compound as a yellow powder (198 mg, 15%). $\delta_H$ (DMSO-$d_6$) 10.11 (1H, s), 8.29 (1H, dd, J 1.5, 4.7 Hz), 7.75 (2H, m), 7.63 (1H, dd, J 1.7, 8.1 Hz), 7.39 (1H, dd, J 8.1, 4.8 Hz), 7.19 (1H, d, J=8.3 Hz), 2.24 (3H, s). LCMS (ES$^+$) RT 3.68 minutes, 392 (M+H)$^+$.

EXAMPLE 19

2-[(4-Bromo-2-fluorophenyl)amino]thieno[2,3-b]pyridine-3-carbonitrile

4-Bromo-2-fluoro-1-isothiocyanatobenzene (250 mg, 1.08 mmol) and (2-chloropyridin-3-yl)acetonitrile (D. H. Bremner et al., *Synthesis*, 1997, 949) (165 mg, 1.08 mmol) were stirred in DMSO (20 mL) and sodium hydride (52 mg, 1.3 mmol) added portionwise. After evolution of gases had finished the reaction mixture was heated for 4 h at 80° C. After this time the reaction mixture was added to ice (50 mL) and a precipitate formed. This was filtered and purified by preparative HPLC (pH 10, 2-3 min) to give the title compound as a white powder (30 mg, 9%). $\delta_H$ (DMSO-$d_6$) 10.45 (1H, s), 8.31 (1H, d, J=3.9 Hz), 7.75 (2H, m), 7.51-7.38 (3H, m). LCMS (ES$^+$) RT 3.49 minutes, 350 (M+H)$^+$.

EXAMPLE 20

2-[(2-Chloro-4-iodophenyl)amino]thieno[2,3-b]pyridine-3-carbonitrile

Intermediate 9 (300 mg, 1.01 mmol) and (2-chloropyridin-3-yl)acetonitrile (D. H. Bremner et al., *Synthesis*, 1997, 949) (165 mg, 1.01 mmol) were stirred together in DMSO (20 mL) and sodium hydride (48 mg, 1.21 mmol) was added portionwise. After evolution of gases was complete the reaction mixture was heated for 4 h at 80° C. After this time the reaction mixture was added to ice (50 mL) and then extracted into DCM (2×50 mL), which was dried (Na$_2$SO$_4$) and evaporated in vacuo to give a yellow residue. This residue was subjected to column chromatography (SiO$_2$, 1:4 EtOAc:hexane) to afford the title compound as a yellow powder (118 mg, 28%). $\delta_H$ (DMSO-$d_6$) 10.38 (1H, s), 8.35 (1H, dd, J 1.5, 4.8 Hz), 8.00 (1H, d, J=1.9 Hz), 7.80 (2H, m), 7.42 (1H, dd, J 8.0, 4.8 Hz), 7.35 (1H, d, J=8.3 Hz). LCMS (ES$^+$) RT 3.70 minutes, 412 (M+H)$^+$.

EXAMPLE 21

2-[(2-Fluoro-4-iodophenyl)amino]thieno[2,3-b]pyridine-3-carboxylic acid (2-amino-2-methylpropyl) amide Trimethylaluminium (2.85 mL of a 2M solution in hexane, 5.7 mmol) was added to a solution of 1,2-diamino-2-methylpropane (498 mg, 5.7 mmol) in toluene (5 mL). After 10 minutes Example 1 (500 mg, 1.13 mmol) was added and the mixture heated at 100° C. for 4 h. After cooling the reaction was quenched with 10% sodium hydroxide solution (75 mL) and extracted with EtOAc (100 mL). The organic phase was dried (Na$_2$SO$_4$) and concentrated in vacuo to give a solid. Trituration with hexanes (30 mL) and filtration gave the title compound as a yellow solid (248 mg, 45%). $\delta_H$ (DMSO-$d_6$) 10.72 (1H, m), 8.43 (1H, dd, J 1.7, 8.0 Hz), 7.84 (1H, dd, J 1.7, 4.7 Hz), 7.80-7.40 (2H, s), 7.46-7.35 (2H, m), 7.21 (1H, m), 7.00 (1H, dd, J 4.7, 8.0 Hz), 3.40 (2H, d, J=5.7 Hz), 1.25 (6H, s). LCMS (ES$^+$) RT 2.23 minutes, 501 (M+H)$^+$.

EXAMPLE 22

2-[(2-Fluoro-4-iodophenyl)amino]thieno[2,3-b]pyridine-3-carboxylic acid [(4R)-2,2-dimethyl-[1,3]-dioxolan-4-ylmethoxy]amide 1-(3-Dimethylaminopropyl)-3-carbodiimide hydrochloride (131 mg, 0.68 mmol) was added to a solution of Intermediate 7 (142 mg, 0.34 mmol), 1-hydroxybenzotriazole (93 mg, 0.68 mmol), N-methylmorpholine (0.10 mL, 0.94 mmol) and (4R)-2,2-dimethyl-[1,31-dioxolan-4-ylmethoxy]amine (WO 02/006213) (101 mg, 0.68 mmol) in N,N-dimethylformamide (5 mL). The reaction mixture was stirred at r.t. for 20 h, then poured into EtOAc (25 mL). The organic solution was washed with sat. brine (2×25 mL), then dried (Na$_2$SO$_4$), filtered and concentrated in vacuo to give a brown solid. The crude product was subjected to column chromatography (SiO$_2$, 2:1 hexanes/EtOAc) to give the title compound as a pale yellow powder (135 mg, 95%). $\delta_H$ (DMSO-$d_6$) 10.98 (1H, s), 8.74 (1H, s), 8.28-8.26 (1H, m), 7.94-7.91 (1H, m), 7.48-7.46 (2H, m), 7.37-7.32 (1H, m), 7.23 (1H, dd, J 4.8, 8.2 Hz), 4.46-4.40 (1H, m), 4.17 (1H, dd, J 3.8, 11.7 Hz), 4.11-4.01 (2H, m), 3.79 (1H, dd, J 7.0, 8.3 Hz), 1.15 (3H, s), 1.10 (3H, s). LCMS RT 3.38 minutes, (ES$^-$) 542 (M–H)$^-$, (ES$^+$) 544 (M+H)$^+$.

EXAMPLE 23

2-[(2-Fluoro-4-iodophenyl)amino]thieno[2,3-b]pyridine-3-carboxylic acid [(2R)-2,3-dihydroxypropoxy] amide A solution of Example 22 (125 mg, 0.23 mmol) in methanol (5 mL) and THF (5 mL) was treated with 10% aq. HCl (5 mL). The reaction mixture was stirred for 3.5 h at r.t., then diluted with EtOAc (25 mL). The organic solution was washed with sat. brine (2×25 mL), then dried (Na$_2$SO$_4$), filtered and concentrated in vacuo to give the title compound as a white powder, which was washed with EtOAc, then hexanes, and dried under suction (76 mg, 66%). $\delta_H$ (DMSO-$d_6$) 11.31 (1H, s), 10.33 (1H, s), 8.34-8.33 (1H, m), 8.12-8.09 (1H, m), 7.79-7.76 (1H, m), 7.63-7.60 (1H, m), 7.45-7.40 (2H, m), 4.89-4.88 (1H, m), 4.62-4.59 (1H, m), 3.99-3.97 (1H, m), 3.85-3.80 (2H, m), 3.43 (2H, m). LCMS RT 3.38 minutes, (ES$^-$) 502 (M–H)$^-$, (ES$^+$) 504 (M+H)$^+$.

EXAMPLE 24

(1-{2-[(2-Fluoro-4-iodophenyl)amino]thieno[2,3-b] pyridine-3-carbonyl}piperidin-4-yl)-carbamic acid tert-butyl ester Prepared from Intermediate 7 (150 mg, 0.36 mmol), 1-hydroxybenzotriazole (98 mg, 0.72 mmol), N-methylmorpholine (0.11 mL, 0.99 mmol), 1-(3-dimethylamino-propyl)-3-carbodiimide hydrochloride (139 mg, 0.72 mmol) and 4-(BOC-amino)-piperidine (145 mg, 0.72 mmol), by the method of Example 22. The title compound was evaporated from ether to give a colourless hard foam (111 mg, 51%). $\delta_H$ (CDCl$_3$, contains rotamers) 9.17 (0.64H, s), 8.90 (0.36H, s), 8.39-8.37 (1H, m), 7.75-7.73 (0.36H, m), 7.66-7.63 (0.64H, m), 7.53-7.50 (2H, m), 7.44-7.39 (1H, m), 7.31-7.28 (1H, m), 4.57 (0.36H, m), 4.40 (0.64H, m), 4.20-4.15 (1.28H, m), 4.03-3.98 (0.72H, m), 3.72 (1H, m), 3.16-3.08 (2H, m), 2.05-2.00 (2H, m), 1.47 (3.2H, s), 1.44 (5.8H, s), 1.36-1.28 (2H, m). LCMS RT 3.36 minutes, (ES$^-$) 595 (M–H)$^-$, (ES$^+$) 597 (M+H)$^+$.

EXAMPLE 25

2-[(2-Fluoro-4-iodophenyl)amino]thieno[2,3-b]pyridine-3-carboxylic acid (4-aminopiperidin-1-yl)amide dihydrochloride A solution of Example 24 (99 mg, 0.17 mmol) in methanol (2 mL) was treated with 4M HCl in 1,4-dioxane (5 mL) and stirred at r.t. for 3 h. The reaction mixture was concentrated in vacuo to give a yellow gum, which was dissolved in water (25 mL). The aqueous solution was washed with ether (2×25 mL), and then evaporated in vacuo. The resulting gum was triturated with ether to give the title compound as a yellow powder (89 mg, 94%). $\delta_H$ (DMSO-$d_6$, contains rotamers) 9.24 (0.5H, s), 9.14 (0.5H, s), 8.38-8.37 (1H, m), 8.13 (3H, br s), 7.82-7.75 (1H, m), 7.72-7.66 (1H, m), 7.55-7.47 (1H, m), 7.38 (1H, dd, J 4.7, 8.1 Hz), 7.23-7.10 (1H, m), 4.02 (2H, br m), 3.25 (1H, br m), 3.06-2.98 (1H, m), 2.88-2.81 (1H, m), 1.93-1.89 (2H, m), 1.43 (2H, br m). LCMS RT 2.86 minutes, (ES$^+$) 497 (M+H)$^+$.

EXAMPLE 26

2-[(2-Fluoro-4-iodophenyl)amino]thieno[2,3-b]pyridine-3-carboxylic acid (2-hydroxy-1-methylethyl) amide Prepared from Intermediate 7 (150 mg, 0.36 mmol), 1-hydroxybenzotriazole (98 mg, 0.72 mmol), N-methylmorpholine (0.11 mL, 0.99 mmol), 1-(3-dimethylamino-propyl)-3-carbodiimide hydrochloride (139 mg, 0.72 mmol) and 2-aminopropanol (0.06 mL, 0.72 mmol), by the method of Example 22. The crude product was subjected to column chromatography (SiO$_2$, 1:1 hexanes/EtOAc) to give the title compound, which was recrystallised from EtOAc/hexanes to give a beige powder (56 mg, 33%). $\delta_H$ (DMSO-$d_6$) 10.45 (1H, s), 8.37-8.36 (1H, m), 8.16-8.13 (1H, m), 7.76-7.71 (2H, m), 7.60-7.57 (1H, m), 7.46-7.36 (2H, m), 4.78 (1H, t, J=5.6 Hz), 4.10-4.03 (1H, m), 3.52-3.35 (2H, m), 1.13 (3H, d, J=6.7 Hz). LCMS RT 3.46 minutes, (ES$^+$) 472 (M+H)$^+$.

EXAMPLE 27

3-[({2-[(2-Fluoro-4-iodophenyl)amino]thieno[2,3-b]pyridine-3-carbonyl}amino)methyl]-azetidine-1-carboxylic acid tert-butyl ester Prepared from Intermediate 7 (150 mg, 0.36 mmol), 1-hydroxybenzotriazole (98 mg, 0.72 mmol), N-methylmorpholine (0.11 mL, 0.99 mmol), 1-(3-dimethylamino-propyl)-3-carbodiimide hydrochloride (139 mg, 0.72 mmol) and 1-BOC-3-(aminomethyl)azetidine (135 mg, 0.72 mmol), by the method of Example 22. The crude product was subjected to column chromatography (SiO$_2$, 3:2 hexanes/EtOAc) to give the title compound, which was recrystallised from ether/hexanes to give a cream-coloured powder (116 mg, 55%). $\delta_H$ (CDCl$_3$) 8.37 (1H, dd, J 1.3, 4.7 Hz), 7.84 (1H, dd, J 1.3, 8.2 Hz), 7.56-7.53 (2H, m), 7.46-7.41 (1H, m), 7.32 (1H, dd, J 4.7, 8.2 Hz), 6.08 (1H, m), 4.14-4.09 (2H, m), 3.77-3.73 (4H, m), 2.94-2.92 (1H, m), 1.46 (9H, s). LCMS RT 3.68 minutes, (ES$^-$) 581 (M−H)$^-$, (ES$^+$) 583 (M+H)$^+$.

EXAMPLE 28

(1-{2-[(2-Fluoro-4-iodophenyl)amino]thieno[2,3-b]pyridine-3-carbonyl}azetidin-3-ylmethyl)carbamic acid tert-butyl ester Prepared from Intermediate 7 (150 mg, 0.36 mmol), 1-hydroxybenzotriazole (98 mg, 0.72 mmol), N-methylmorpholine (0.11 mL, 0.99 mmol), 1-(3-dimethylamino-propyl)-3-carbodiimide hydrochloride (139 mg, 0.72 mmol) and 3-(BOC-aminomethyl)-azetidine (135 mg, 0.72 mmol), by the method of Example 22. The title compound was evaporated from ether to give a colourless hard foam (75 mg, 36%). $\delta_H$ (CDCl$_3$) 8.25 (1H, dd, J 1.5, 4.7 Hz), 7.67 (1H, dd, J 1.5, 8.1 Hz), 7.46-7.41 (2H, m), 7.38-7.33 (1H, m), 7.22 (1H, dd, J 4.7, 8.1 Hz), 4.59 (1H, br s), 4.15-4.09 (2H, m), 3.80-3.75 (2H, m), 3.32 (2H, m), 2.78-2.74 (1H, m), 1.35 (9H, s). LCMS RT 3.41 minutes, (ES$^-$) 581 (M−H)$^-$, (ES$^+$) 583 (M+H)$^+$.

EXAMPLE 29

3-({2-[(2-Fluoro-4-iodophenyl)amino]thieno[2,3-b]pyridine-3-carbonyl}amino)azetidine-1-carboxylic acid tert-butyl ester Prepared from Intermediate 7 (150 mg, 0.36 mmol), 1-hydroxybenzotriazole (98 mg, 0.72 mmol), N-methylmorpholine (0.11 mL, 0.99 mmol), 1-(3-dimethylamino-propyl)-3-carbodiimide hydrochloride (139 mg, 0.72 mmol) and 1-BOC-3-aminoazetidine (125 mg, 0.72 mmol), by the method of Example 22. The title compound was recrystallised from ether/hexanes to give a cream-coloured powder (116 mg, 57%). $\delta_H$ (CDCl$_3$) 8.38 (1H, dd, J 1.2, 4.7 Hz), 7.90 (1H, dd, J 1.2, 8.1 Hz), 7.56-7.53 (2H, m), 7.45-7.40 (1H, m), 7.35 (1H, dd, J 4.7, 8.1 Hz), 6.19 (1H, d, J=6.9 Hz), 4.89-4.84 (1H, m), 4.44-4.38 (2H, m), 3.93-3.88 (2H, m), 1.48 (9H, s). LCMS RT 3.66 minutes, (ES$^-$) 567 (M−H)$^-$, (ES$^+$) 569 (M+H)$^+$.

EXAMPLE 30

[3-(Aminomethyl)azetidin-1-yl]-{2-[(2-fluoro-4-iodophenyl)amino]thieno[2,3-b]pyridin-3-yl}-methanone A solution of Example 28 (65 mg, 0.11 mmol) in DCM (7 mL) was treated with trifluoroacetic acid (3 mL) and stirred for 1 h at r.t. The reaction mixture was concentrated in vacuo to give a yellow gum, which was dissolved in water (25 mL) and basified to pH 10 with sodium carbonate. The aqueous solution was extracted with 5% methanol in DCM (4×25 mL), and the extracts combined, then dried (Na$_2$SO$_4$), filtered and concentrated in vacuo. The crude product was subjected to column chromatography (SiO$_2$, 4:1 DCM/methanol) to give the title compound as a gummy solid, which was triturated from ether to give a cream-coloured powder (34 mg, 63%). $\delta_H$ (DMSO-d$_6$) 8.31 (1H, m), 7.93 (1H, m), 7.72 (1H, dd, J 1.5, 10.5 Hz), 7.55 (1H, m), 7.37 (1H, dd, J 4.6, 8.1 Hz), 7.29-7.24 (1H, m), 4.88 (2H, br s), 4.03-3.97 (2H, m), 3.71-3.67 (2H, m), 2.65 (1H, m), 2.70-2.68 (2H, m). LCMS RT 2.93 minutes, (ES$^-$) 481 (M−H)$^-$, (ES$^+$) 483 (M+H)$^+$.

EXAMPLE 31

2-[(2-Fluoro-4-iodophenyl)amino]thieno[2,3-b]pyridine-3-carboxylic acid [(2R)-pyrrolidin-2-ylmethyl] amide A solution of Intermediate 10 (135 mg, 0.23 mmol) in methanol (2 ml) was treated with 4M HCl in 1,4-dioxane (5 mL) and stirred at r.t. for 30 min. The reaction mixture was concentrated in vacuo to give a yellow gum, which was dissolved in water (25 mL). The aqueous solution was washed with ether (2×25 mL), then basified to pH 11 with 25% aq. ammonium hydroxide. The aqueous solution was extracted with DCM (2×25 mL), and the organic extracts combined, dried (Na$_2$SO$_4$), filtered and concentrated in vacuo. The crude product was subjected to column chromatography (SiO$_2$, 91:8:1 DCM/methanol/25% aq. ammonium hydroxide) to give the title compound, which was freeze-dried overnight from acetonitrile/water to give a cream-coloured powder (73 mg, 65%). $\delta_H$ (DMSO-d$_6$) 10.63 (1H, s), 9.12 (1H, br s), 8.37 (1H, dd, J 1.7, 8.0 Hz), 7.84 (1H, dd, J 1.7, 4.7 Hz), 7.47 (1H, dd, J 2.0, 10.4 Hz), 7.42-7.38 (1H, m), 7.17-7.11 (1H, m), 7.00 (1H, dd, J 4.7, 8.0 Hz), 3.68-3.61 (1H, m), 3.51-3.49 (2H, m), 3.17-3.12 (2H, m), 2.28-1.62 (4H, m). LCMS RT 2.42 minutes, (ES$^-$) 495 (M−H)$^-$, (ES$^+$) 497 (M+H)$^+$.

EXAMPLE 32

2-[(2-Fluoro-4-iodophenyl)amino]thieno[2,3-b]pyridine-3-carboxylic acid [(2S)-pyrrolidin-2-ylmethyl] amide Prepared from Intermediate 11 (139 mg, 0.23 mmol) by the method of Example 31. The title compound was obtained as a cream-coloured powder (81 mg, 70%). $\delta_H$ (DMSO-d$_6$) 10.63 (1H, s), 9.12 (1H, br s), 8.37 (1H, dd, J 1.7, 8.0 Hz), 7.84 (1H, dd, J 1.7, 4.7 Hz), 7.47 (1H, dd, J 2.0, 10.4 Hz), 7.42-7.38 (1H, m), 7.17-7.11 (1H, m), 7.00 (1H, dd, J 4.7, 8.0 Hz), 3.68-3.61 (1H, m), 3.51-3.49 (2H, m), 3.17-3.12 (2H, m), 2.28-1.62 (4H, m). LCMS RT 2.42 minutes, (ES$^-$) 495 (M−H)$^-$, (ES$^+$) 497 (M+H)$^+$.

EXAMPLE 33

(3S)-3-({2-[(2-Fluoro-4-iodophenyl)amino]thieno[2,3-b]pyridine-3-carbonyl}amino)-piperidine-1-carboxylic acid tert-butyl ester Prepared from Intermediate 7 (150 mg, 0.36 mmol), 1-hydroxybenzotriazole (98 mg, 0.72 mmol), N-methylmorpholine (0.11 mL, 0.99 mmol), 1-(3-dimethylamino-propyl)-3-carbodiimide hydrochloride (139 mg, 0.72 mmol) and (S)-1-BOC-3-aminopiperidine (145 mg, 0.72 mmol), by the method of Example 22. The title compound was obtained as a gummy yellow solid (131 mg, 61%). $\delta_H$ (CDCl$_3$) 11.34 (1H, s), 8.36-8.34 (1H, m), 7.90-7.88 (1H, m), 7.55-7.52 (2H, m), 7.45-7.42 (1H, m), 7.32-7.29 (1H, m), 5.32 (1H, br s), 4.31 (1H, m), 3.83-3.78 (2H, m), 3.46-3.42 (1H, m), 3.17 (1H, m), 1.89-1.73 (2H, m), 1.67 (2H, m), 1.47 (9H, s). LCMS RT 4.04 minutes, (ES$^+$) 597 (M+H)$^+$.

EXAMPLE 34

(3R)-3-({2-[(2-Fluoro-4-iodophenyl)amino]thieno[2,3-b]pyridine-3-carbonyl}amino)-piperidine-1-carboxylic acid tert-butyl ester Prepared from Intermediate 7 (150 mg, 0.36 mmol), 1-hydroxybenzotriazole (98 mg, 0.72 mmol), N-methylmorpholine (0.11 mL, 0.99 mmol), 1-(3-dimethylamino-propyl)-3-carbodiimide hydrochloride (139 mg, 0.72 mmol) and (R)-1-BOC-3-aminopiperidine (145 mg, 0.72 mmol), by the method of Example 22. The title compound was obtained as a pale pink gummy solid (136 mg, 63%). $\delta_H$ (CDCl$_3$) 11.34 (1H, s), 8.36-8.34 (1H, m), 7.90-7.88 (1H, m), 7.55-7.52 (2H, m), 7.45-7.42 (1H, m), 7.32-7.29 (1H, m), 5.32 (1H, br s), 4.31 (1H, m), 3.83-3.78 (2H, m), 3.46-3.42 (1H, m), 3.17 (1H, m), 1.89-1.73 (2H, m), 1.67 (2H, m), 1.47 (9H, s). LCMS RT 4.03 minutes, (ES$^+$) 597 (M+H)$^+$.

EXAMPLE 35

2-[(2-Fluoro-4-iodophenyl)amino]thieno[2,3-b]pyridine-3-carboxylic acid [(3S)-piperidin-3-yl]amide dihydrochloride A solution of Example 33 (120 mg, 0.20 mmol) in methanol (2 mL) was treated with 4M HCl in 1,4-dioxane (5 mL) and stirred at r.t. for 3 h. The reaction mixture was evaporated in vacuo to give the title compound as a gummy yellow solid, which was triturated from ether to give a yellow powder (112 mg, 98%). $\delta_H$ (DMSO-d$_6$) 10.38 (1H, s), 9.04-8.92 (2H, m), 8.38 (1H, dd, J 1.3, 4.6 Hz), 8.17-8.14 (2H, m), 7.75 (1H, dd, J 1.8, 10.4 Hz), 7.61-7.58 (1H, m), 7.44 (1H, dd, J 4.6, 8.2 Hz), 7.42-7.36 (1H, m), 4.09 (1H, m), 3.34-3.31 (1H, m), 3.21-3.17 (1H, m), 2.94-2.79 (2H, m), 1.91 (2H, m), 1.74-1.61 (2H, m). LCMS RT 2.38 minutes, (ES$^+$) 497 (M+H)$^+$.

EXAMPLE 36

2-[(2-Fluoro-4-iodophenyl)amino]thieno[2,3-b]pyridine-3-carboxylic acid [(3R)-piperidin-3-yl]amide dihydrochloride Prepared from Example 34 (126 mg, 0.21 mmol) by the method of Example 35. The title compound was obtained as a yellow powder (115 mg, 96%). $\delta_H$ (DMSO-d$_6$) 10.38 (1H, s), 9.04-8.92 (2H, m), 8.38 (1H, dd, J 1.3, 4.6 Hz), 8.17-8.14 (2H, m), 7.75 (1H, dd, J 1.8, 10.4 Hz), 7.61-7.58 (1H, m), 7.44 (1H, dd, J 4.6, 8.2 Hz), 7.42-7.36 (1H, m), 4.09 (1H, m), 3.34-3.31 (1H, m), 3.21-3.17 (1H, m), 2.94-2.79 (2H, m), 1.91 (2H, m), 1.74-1.61 (2H, m). LCMS RT 2.38 minutes, (ES$^+$) 497 (M+H)$^+$.

EXAMPLE 37

(1-{2-[(2-Fluoro-4-iodophenyl)amino]thieno[2,3-b]pyridine-3-carbonyl}-(3R)-pyrrolidin-3-yl)carbamic acid tert-butyl ester Prepared from Intermediate 7 (150 mg, 0.36 mmol), 1-hydroxybenzotriazole (98 mg, 0.72 mmol), N-methylmorpholine (0.11 mL, 0.99 mmol), 1-(3-dimethylamino-propyl)-3-carbodiimide hydrochloride (139 mg, 0.72 mmol) and (R)-3-(BOC-amino)-pyrrolidine (186 mg, 0.72 mmol), by the method of Example 22. The crude product was subjected to column chromatography (SiO$_2$, 3:2 hexanes/EtOAc) to give the title compound, which was evaporated from ether to give a colourless hard foam (110 mg, 52%). $\delta_H$ (CDCl$_3$) 9.03 (1H, s), 8.28 (1H, dd, J 1.5, 4.7 Hz), 7.56 (1H, dd, J 1.5, 8.1 Hz), 7.43-7.39 (2H, m), 7.34-7.29 (1H, m), 7.22-7.18 (1H, m), 4.50 (1H, br s), 4.16-4.14 (1H, m), 3.71 (1H, dd, J 6.2, 11.8 Hz), 3.63-3.56 (2H, m), 3.30 (1H, dd, J 5.1, 11.8 Hz), 2.19-2.12 (1H, m), 1.86-1.77 (1H, m), 1.35 (9H, s). LCMS RT 3.33 minutes, (ES$^-$) 581
(M−H)$^-$, (ES$^+$) 583 (M+H)$^+$.

EXAMPLE 38

(1-{2-[(2-Fluoro-4-iodophenyl)amino]thieno[2,3-b]pyridine-3-carbonyl}-(3S)-pyrrolidin-3-yl)carbamic acid tert-butyl ester Prepared from Intermediate 7 (150 mg, 0.36 mmol), 1-hydroxybenzotriazole (98 mg, 0.72 mmol), N-methylmorpholine (0.11 mL, 0.99 mmol), 1-(3-dimethylamino-propyl)-3-carbodiimide hydrochloride (139 mg, 0.72 mmol) and (S)-3-(BOC-amino)-pyrrolidine (186 mg, 0.72 mmol), by the method of Example 37. The title compound was obtained as a colourless hard foam (125 mg, 59%). $\delta_H$ (CDCl$_3$) 9.03 (1H, s), 8.28 (1H, dd, J 1.5, 4.7 Hz), 7.56 (1H, dd, J 1.5, 8.1 Hz), 7.43-7.39 (2H, m), 7.34-7.29 (1H, m), 7.22-7.18 (1H, m), 4.50 (1H, br s), 4.16-4.14 (1H, m), 3.71 (1H, dd, J 6.2, 11.8 Hz), 3.63-3.56 (2H, m), 3.30 (1H, dd, J 5.1, 11.8 Hz), 2.19-2.12 (1H, m), 1.86-1.77 (1H, m), 1.35 (9H, s). LCMS RT 3.33 minutes, (ES$^-$) 581 (M−H)$^-$, (ES$^+$) 583 (M+H)$^+$.

EXAMPLE 39

(1-{2-[(2-Fluoro-4-iodophenyl)amino]thieno[2,3-b]pyridine-3-carbonyl}azetidin-3-yl)-carbamic acid tert-butyl ester Prepared from Intermediate 7 (150 mg, 0.36 mmol), 1-hydroxybenzotriazole (98 mg, 0.72 mmol), N-methylmorpholine (0.11 mL, 0.99 mmol), 1-(3-dimethylamino-propyl)-3-carbodiimide hydrochloride (139 mg, 0.72 mmol) and 3-(BOC-amino)azetidine (125 mg, 0.72 mmol), by the method of Example 22. The crude product was subjected to column chromatography (SiO$_2$, 3:1 hexanes/EtOAc) to give the title compound, which was evaporated from ether to a cream-coloured powder (100 mg, 49%). $\delta_H$ (CDCl$_3$) 10.11 (1H, s), 8.35 (1H, dd, J 1.5, 4.7 Hz), 7.76 (1H, dd, J 1.5, 8.1 Hz), 7.55-7.51 (2H, m), 7.47-7.41 (1H, m), 7.31 (1H, dd, J 4.7. 8.1 Hz), 4.95 (1H, br s), 4.52 (1H, br s), 4.46-4.40 (2H, m), 4.01-3.96 (2H, m), 1.45 (9H, s). LCMS RT 3.47 minutes, (ES$^-$) 567 (M−H)$^-$, (ES$^+$) 569 (M+H)$^+$.

EXAMPLE 40

4-({2-[(2-Fluoro-4-iodophenyl)amino]thieno[2,3-b]pyridine-3-carbonyl}amino)-piperidine-1-carboxylic acid tert-butyl ester Prepared from Intermediate 7 (150 mg, 0.36 mmol), 1-hydroxybenzotriazole (98 mg, 0.72 mmol), N-methylmorpholine (0.11 mL, 0.99 mmol), 1-(3-dimethylamino-propyl)-3-carbodiimide hydrochloride (139 mg, 0.72 mmol) and 4-amino-1-BOC-piperidine (145 mg, 0.72 mmol), by the method of Example 22. The crude product was adsorbed onto $SiO_2$ and subjected to column chromatography ($SiO_2$, 2:1 hexanes/EtOAc) to give the title compound, which was evaporated from ether to give cream-coloured flakes (97 mg, 45%). $\delta_H$ (CDCl$_3$) 11.18 (1H, s), 8.36 (1H, dd, J 1.4, 4.7 Hz), 7.81 (1H, dd, J 1.4, 8.2 Hz), 7.55-7.53 (2H, m), 7.46-7.41 (1H, m), 7.32 (1H, dd, J 4.7. 8.2 Hz), 5.74 (1H, d, J=7.6 Hz), 4.27-4.20 (1H, m), 4.15-4.11 (2H, m), 3.03-2.96 (2H, m), 2.15-2.10 (2H, m), 1.50 (9H, s), 1.45 (2H, m). LCMS RT 3.95 minutes, (ES$^-$) 567 (M−H)$^-$, (ES$^+$) 569 (M+H)$^+$.

EXAMPLE 41

[(3R)-3-Aminopyrrolidin-1-yl]-{2-[(2-fluoro-4-iodophenyl)amino]thieno[2,3-b]pyridin-3-yl}-methanone Prepared from Example 37 (100 mg, 0.17 mmol) following the method of Example 35. The title compound was obtained as a yellow powder (100 mg, quant.). $\delta_H$ (DMSO-d$_6$) 9.29 (1H, s), 8.36 (1H, dd, J 1.5, 4.7 Hz), 8.29 (3H, s), 7.91-7.89 (1H, m), 7.72 (1H, dd, J 1.8, 10.4 Hz), 7.55-7.52 (1H, m), 7.37 (1H, dd, J 4.7, 8.1 Hz), 7.24-7.19 (1H, m), 3.79-3.72 (1H, m), 3.70-3.58 (2H, m), 3.51-3.38 (2H, m), 2.20-2.13 (1H, m), 2.01-1.97 (1H, m). LCMS RT 2.24 minutes, (ES$^-$) 481 (M−H)$^-$, (ES$^+$) 483 (M+H)$^+$.

EXAMPLE 42 [(3S)-3-Aminopyrrolidin-1-yl]-{2-[(2-fluoro-4-iodophenyl)amino]thieno[2,3-b]pyridin-3-yl}-methanone Prepared from Example 38 (115 mg, 0.20 mmol) following the method of Example 35. The title compound was obtained as a yellow powder (109 mg, 99%). $\delta_H$ (DMSO-d$_6$) 9.29 (1H, s), 8.36 (1H, dd, J 1.5, 4.7 Hz), 8.29 (3H, s), 7.91-7.89 (1H, m), 7.72 (1H, dd, J 1.8, 10.4 Hz), 7.55-7.52 (1H, m), 7.37 (1H, dd, J 4.7, 8.1 Hz), 7.24-7.19 (1H, m), 3.79-3.72 (1H, m), 3.70-3.58 (2H, m), 3.51-3.38 (2H, m), 2.20-2.13 (1H, m), 2.01-1.97 (1H, m). LCMS RT 2.24 minutes, (ES$^-$) 481 (M−H)$^-$, (ES$^+$) 483 (M+H)$^+$.

EXAMPLE 43

2-[(2-Fluoro-4-iodophenyl)amino]thieno[2,3-b]pyridine-3-carboxylic acid (piperidin-4-yl)amide Prepared from Example 40 (87 mg, 0.15 mmol) following the method of Example 35.
The title compound was obtained as a yellow powder (80 mg, 96%). $\delta_H$ (DMSO-d$_6$) 10.31 (1H, s), 8.84 (1H, m), 8.68 (1H, m), 8.38 (1H, dd, J 1.3, 4.6 Hz), 8.24 (1H, d, J 7.5 Hz), 8.09 (1H, dd, J 1.3, 8.2 Hz), 7.74 (1H, dd, J 1.8, 10.5 Hz), 7.59-7.57 (1H, m), 7.44 (1H, dd, J 4.7, 8.2 Hz), 7.39-7.34 (1H, m), 4.05-3.97 (1H, m), 3.32-3.27 (2H, m), 3.03-2.87 (2H, m), 2.00-1.97 (2H, m), 1.82-1.71 (2H, m). LCMS RT 2.40 minutes, (ES$^-$) 495 (M−H)$^-$, (ES$^+$) 497 (M+H)$^+$.

EXAMPLE 44

(3-Aminoazetidin-1-yl)-{2-[(2-fluoro-4-iodophenyl)amino]thieno[2,3-b]pyridin-3-yl]-methanone Prepared from Example 39 (90 mg, 0.16 mmol) by the method of Example 30. The reaction mixture was concentrated in vacuo to give a yellow gum, which was dissolved in methanol (5 mL) and water (5 mL) and basified to pH 10 with 25% aq. ammonium hydroxide. The aqueous solution was concentrated in vacuo onto $SiO_2$, and the crude product was subjected to column chromatography ($SiO_2$, 95:4:1 DCM/methanol/25% aq. ammonium hydroxide). The title compound was freeze-dried overnight from acetonitrile/methanol/water to give a cream-coloured powder (31 mg, 42%). $\delta_H$ (DMSO-d$_6$) 8.33 (1H, dd, J 1.5, 4.7 Hz), 7.94 (1H, dd, J 1.5, 8.1 Hz), 7.73 (1H, dd, J 1.9, 10.5 Hz), 7.54 (1H, ddd, J 0.9, 0.9, 8.4 Hz), 7.38 (1H, dd, J 4.7, 8.1 Hz), 7.31-7.26 (1H, m), 4.23-4.11 (2H, m), 3.72-3.59 (3H, m). LCMS RT 3.00 minutes, (ES$^-$) 467 (M−H)$^-$, (ES$^+$) 469 (M+H)$^+$.

EXAMPLE 45

2-[(2-Fluoro-4-iodophenyl)amino]thieno[2,3-b]pyridine-3-carboxylic acid bis(2-hydroxy-ethyl)amide Prepared from Intermediate 7 (150 mg, 0.36 mmol), 1-hydroxybenzotriazole (98 mg, 0.72 mmol), N-methylmorpholine (0.11 mL, 0.99 mmol), 1-(3-dimethylamino-propyl)-3-carbodiimide hydrochloride (139 mg, 0.72 mmol) and diethanolamine (76 mg, 0.72 mmol), by the method of Example 22. The crude product was subjected to column chromatography ($SiO_2$, EtOAc, twice) to give the title compound, which was freeze-dried overnight from acetonitrile/water to give a cream-coloured powder (62 mg, 34%). $\delta_H$ (DMSO-d$_6$) 8.79 (1H, br s), 8.38 (1H, dd, J 1.5, 4.7 Hz), 7.77 (1H, dd, J 1.5, 8.1 Hz), 7.67 (1H, dd, J 1.9, 10.5 Hz), 7.69-7.46 (1H, m), 7.38 (1H, dd, J 4.7, 8.1 Hz), 7.18-7.12 (1H, m), 4.83 (2H, br s), 3.30 (8H, s). LCMS RT 3.01 minutes, (ES$^+$) 502 (M+H)$^+$.

EXAMPLE 46

{2-[(2-Fluoro-4-iodophenyl)amino]thieno[2,3-b]pyridin-3-yl}-(3-hydroxyazetidin-1-yl)-methanone Prepared from Intermediate 7 (225 mg, 0.54 mmol), 1-hydroxybenzotriazole (147 mg, 1.08 mmol), N-methylmorpholine (0.16 mL, 1.48 mmol), 1-(3-dimethylamino-propyl)-3-carbodiimide hydrochloride (208 mg, 1.08 mmol) and 3-hydroxyazetidine hydrochloride (120 mg, 1.08 mmol), by the method of Example 22. After chromatography, the title compound was recrystallised from methanol/ether to give a white powder (125 mg, 49%). $\delta_H$ (DMSO-d$_6$) 9.60 (1H, s), 8.35-8.34 (1H, m), 7.94 (1H, dd, J 1.4, 8.1 Hz), 7.75-7.71 (1H, m), 7.57-7.54 (1H, m), 7.41-7.37 (1H, m), 7.31-7.25 (1H, m), 5.68 (1H, d, J=6.0 Hz), 4.47-4.44 (1H, m), 4.21-4.16 (2H, m), 3.79-3.74 (2H, m). LCMS RT 3.31 minutes, (ES$^+$) 470 (M+H)$^+$.

EXAMPLE 47

{2-[(2-Fluoro-4-iodophenyl)amino]thieno[2,3-b]pyridin-3-yl}-[(3R)-3-hydroxypyrrolidin-1-yl]-methanone Prepared from Intermediate 7 (150 mg, 0.36 mmol), 1-hydroxybenzotriazole (98 mg, 0.72 mmol), N-methylmorpholine (0.11 mL, 0.99 mmol), 1-(3-dimethylamino-propyl)-3-carbodiimide hydrochloride (139 mg, 0.72 mmol) and (R)-3-hydroxy-pyrrolidine (63 mg, 0.72 mmol), by the method of Example 22. After chromatography, the title compound was freeze-dried overnight from acetonitrile/water to give a cream-coloured powder (116 mg, 66%). $\delta_H$ (DMSO-$d_6$) 9.20 (1H, s), 8.35 (1H, dd, J 1.5, 4.7 Hz), 7.81 (1H, dd, J 1.5, 8.1 Hz), 7.67 (1H, dd, J 1.9, 10.5 Hz), 7.50-7.47 (1H, m), 7.36 (1H, dd, J 4.7, 8.1 Hz), 7.17-7.11 (1H, m), 4.91 (1H, s), 4.22 (1H, s), 3.54-3.30 (3H, m), 3.21-3.17 (1H, m), 1.90-1.74 (2H, m). LCMS RT 3.18 minutes, (ES$^+$) 484 (M+H)$^+$.

EXAMPLE 48

{2-[(2-Fluoro-4-iodophenyl)amino]thieno[2,3-b]pyridin-3-yl}-[(3S)-3-hydroxypyrrolidin-1-yl]-methanone Prepared from Intermediate 7 (150 mg, 0.36 mmol), 1-hydroxybenzotriazole (98 mg, 0.72 mmol), N-methylmorpholine (0.11 mL, 0.99 mmol), 1-(3-dimethylamino-propyl)-3-carbodiimide hydrochloride (139 mg, 0.72 mmol) and (S)-3-hydroxypyrrolidine (63 mg, 0.72 mmol), by the method of Example 47. The title compound was obtained as a cream-coloured powder (105 mg, 60%). $\delta_H$ (DMSO-$d_6$) 9.20 (1H, s), 8.35 (1H, dd, J 1.5, 4.7 Hz), 7.81 (1H, dd, J 1.5, 8.1 Hz), 7.67 (1H, dd, J 1.9, 10.5 Hz), 7.50-7.47 (1H, m), 7.36 (1H, dd, J 4.7, 8.1 Hz), 7.17-7.11 (1H, m), 4.91 (1H, s), 4.22 (1H, s), 3.54-3.30 (3H, m), 3.21-3.17 (1H, m), 1.90-1.74 (2H, m). LCMS RT 3.17 minutes, (ES$^+$) 484 (M+H)$^+$.

EXAMPLE 49

{2-[(2-Fluoro-4-iodophenyl)amino]thieno[2,3-b]pyridin-3-yl}-[2-(hydroxymethyl)-piperidin-1-yl]-methanone Prepared from Intermediate 7 (150 mg, 0.36 mmol), 1-hydroxybenzotriazole (98 mg, 0.72 mmol), N-methylmorpholine (0.11 mL, 0.99 mmol), 1-(3-dimethylamino-propyl)-3-carbodiimide hydrochloride (139 mg, 0.72 mmol) and 2-piperidinemethanol (83 mg, 0.72 mmol), by the method of Example 22. After chromatography, the title compound was recrystallised from EtOAc/hexanes to give a pale yellow powder (44 mg, 24%). $\delta_H$ (DMSO-$d_6$, 130° C.) 8.38 (1H, dd, J 1.5, 4.7 Hz), 7.83 (1H, dd, J 1.5, 8.0 Hz), 7.59 (1H, dd, J 1.9, 10.5 Hz), 7.47 (1H, d, J=8.5 Hz), 7.35 (1H, dd, J 4.7, 8.0 Hz), 7.16 (1H, dd, J 8.8, 8.8 Hz), 4.30 (1H, br s), 4.21 (1H, m), 3.89 (1H, m), 3.65-3.60 (1H, m), 3.51-3.47 (1H, m), 3.03-2.97 (1H, m), 1.74-1.72 (1H, m), 1.65-1.56 (4H, m), 1.37 (1H, m). LCMS RT 2.86 minutes, (ES$^-$) 510 (M–H)$^-$, (ES$^+$) 512 (M+H)$^+$.

EXAMPLE 50

{2-[(2-Fluoro-4-iodophenyl)amino]thieno[2,3-b]pyridin-3-yl}-[(3S)-3-(hydroxymethyl)-morpholin-4-yl]-methanone Prepared from Intermediate 7 (150 mg, 0.36 mmol), 1-hydroxybenzotriazole (98 mg, 0.72 mmol), N-methylmorpholine (0.11 mL, 0.99 mmol), 1-(3-dimethylamino-propyl)-3-carbodiimide hydrochloride (139 mg, 0.72 mmol) and (3S)-3-(hydroxymethyl)-morpholine (85 mg, 0.72 mmol), by the method of Example 22. After chromatography, the title compound was freeze-dried overnight from acetonitrile/water to give a cream-coloured powder (81 mg, 44%). $\delta_H$ (DMSO-$d_6$, 120° C.) 8.37-8.36 (1H, m), 7.85-7.83 (1H, m), 7.60 (1H, dd, J 1.8, 10.5 Hz), 7.49-7.47 (1H, m), 7.35 (1H, dd, J 4.7, 8.0 Hz), 7.15 (1H, dd, J 8.7, 8.7 Hz), 3.99 (1H, m), 3.85 (1H, d, J=11.6 Hz), 3.80-3.77 (1H, m), 3.70-3.67 (1H, m), 3.65-3.56 (2H, m), 3.48-3.45 (1H, m), 3.34 (1H, m), 3.27-3.21 (1H, m). LCMS RT 2.60 minutes, (ES$^-$) 512 (M–H)$^-$, (ES$^+$) 514 (M+H)$^+$.

EXAMPLE 51

4-{2-[(2-Fluoro-4-iodophenyl)amino]thieno[2,3-b]pyridine-3-carbonyl}-(3R)-3-(hydroxymethyl)piperazine-1-carboxylic acid tert-butyl ester Prepared from Intermediate 7 (150 mg, 0.36 mmol), 1-hydroxybenzotriazole (98 mg, 0.72 mmol), N-methylmorpholine (0.11 mL, 0.99 mmol), 1-(3-dimethylamino-propyl)-3-carbodiimide hydrochloride (139 mg, 0.72 mmol) and (2R)-4-BOC-2-(hydroxymethyl)piperazine (157 mg, 0.72 mmol), by the method of Example 22. The crude product was subjected to column chromatography (SiO$_2$, 1:1 hexanes/EtOAc) to give the title compound, which was evaporated from ether to give a pale pink, hard foam (95 mg, 43%). $\delta_H$ (DMSO-$d_6$, 120° C.) 8.53 (1H, br s), 8.38-8.37 (1H, m), 7.86-7.84 (1H, m), 7.60 (1H, dd, J 1.7, 10.5 Hz), 7.49 (1H, d, J=8.5 Hz), 7.36 (1H, dd, J 4.7, 8.0 Hz), 7.19-7.15 (1H, dd, J 8.5, 8.7 Hz), 4.52 (1H, br s), 4.16 (1H, m), 3.95 (1H, d, J=13.5 Hz), 3.88-3.81 (2H, m), 3.49-3.43 (2H, m), 3.14-3.10 (1H, m), 3.02-2.95 (1H, m), 1.43 (9H, s). LCMS RT 2.98 minutes, (ES$^+$) 613 (M+H)$^+$.

EXAMPLE 52

2-[(2-Fluoro-4-iodophenyl)amino]thieno[2,3-b]pyridine-7-oxide

Example 8 (250 mg, 0.55 mmol) was suspended in a mixture of ethanol (20 mL) and water (10 mL). Lithium hydroxide hydrate (24.0 mg, 0.57 mmol) was added and the mixture heated to reflux for 24 hours. After concentration and freeze-drying, the mixture was purified by chromatography (silica, dichloromethane then 2% MeOH in dichloromethane). The title compound was obtained as an off-white solid (50 mg, 24%). $\delta_H$ (DMSO-$d_6$) 9.42 (1H, br s), 8.13 (1H, dd, J 0.7, 6.2 Hz), 7.69 (1H, dd, J 1.9, 10.7 Hz), 7.54-7.51 (2H, m), 7.39-7.32 (2H, m), 6.73 (1H, s). LCMS (ES$^+$) RT 2.84 minutes, 387 (M+H)$^+$.

EXAMPLE 53

2-[(2-Fluoro-4-iodophenyl)amino]-N-[2-(morpholin-4-yl)ethyl]thieno[2,3-b]pyridine-3-carboxamide Prepared from Example 1 (250 mg, 0.56 mmol) and 4-(2-aminoethyl)morpholine (292 mg, 2.24 mmol) by the method of Example 5. After chromatography (5% methanol, 95% dichloromethane) the title compound was obtained as an off-white solid (140 mg, 47%). $\delta_H$ (CDCl$_3$) 11.43 (1H, br s), 8.36 (1H, dd, J 1.4, 4.7 Hz), 8.03 (1H, dd, J 1.4, 8.2 Hz), 7.55-7.51 (2H, m), 7.44 (1H, dd, J 8.2, 8.2 Hz), 7.32 (1H, dd, J 4.7, 8.2

Hz), 6.84 (1H, br s), 3.80-3.77 (4H, m), 3.67-3.62 (2H, m), 2.73-2.69 (2H, m), 2.62-2.59 (4H, m). LCMS (ES$^+$) RT 2.37 minutes, 527 (M+H)$^+$.

EXAMPLE 54

2-[4-({2-[(2-Fluoro-4-iodophenyl)amino]thieno[2,3-b]pyridin-3-yl}carbonyl)piperazin-1-yl]ethanol Prepared from Example 1 (250 mg, 0.56 mmol) and N-(2-hydroxyethyl)piperazine (292 mg, 2.24 mmol) by the method of Example 5. After chromatography (5% methanol, 95% dichloromethane) the title compound was obtained as a white solid (86 mg, 29%). $\delta_H$ (DMSO-d$_6$) 9.13 (1H, br s), 8.36 (1H, dd, J 1.5, 4.7 Hz), 7.80 (1H, dd, J 1.5, 8.1 Hz), 7.68 (1H, dd, J 1.9, 10.5 Hz), 7.49-7.45 (1H, m), 7.37 (1H, dd, J 4.7, 8.1 Hz), 7.10 (1H, dd, J 8.7, 8.7 Hz), 4.37 (1H, t, J=5.4 Hz), 3.50-3.40 (6H, m), 2.37-2.33 (6H, m). LCMS (ES$^+$) RT 2.16 minutes, 527 (M+H)$^+$.

EXAMPLE 55

3-(1,4-Diazepan-1-ylcarbonyl)-N-(2-fluoro-4-iodophenyl)thieno[2,3-b]pyridin-2-amine Prepared from Example 1 (250 mg, 0.56 mmol) and homopiperazine (224 mg, 2.24 mmol) by the method of Example 5. After chromatography (10-15% methanol in dichloromethane) the title compound was obtained as a pale yellow solid (180 mg, 64%). $\delta_H$ (CDCl$_3$) 8.99 (1H, br s), 8.34 (1H, dd, J 1.6, 4.7 Hz), 7.74 (1H, dd, J 1.6, 8.1 Hz), 7.47-7.43 (2H, m), 7.35 (1H, dd, J 8.5, 8.5 Hz), 7.28-7.22 (1H, m), 4.30-4.10 (1H, br m), 3.95-3.80 (1H, br m), 3.39-2.86 (6H, br m), 2.17-1.77 (3H, br m). LCMS (ES$^+$) RT 2.17 minutes, 497 (M+H)$^+$.

EXAMPLE 56

N-[3-(Dimethylamino)-2,2-dimethylpropyl]-2-[(2-fluoro-4-iodophenyl)amino]thieno[2,3-b]pyridine-3-carboxamide Prepared from Example 1 (250 mg, 0.56 mmol) and N,N,2,2-tetramethyl-1,3-propanediamine (292 mg, 2.24 mmol) by the method of Example 5. After chromatography (5% methanol, 95% dichloromethane) the title compound was obtained as a pale yellow solid (60 mg, 20%). $\delta_H$ (DMSO-d$_6$) 10.81 (1H, br s), 9.10 (1H, br s), 8.24-8.21 (2H, m), 7.69-7.65 (1H, m), 7.55-7.52 (1H, m), 7.37-7.31 (2H, m), 3.29-3.27 (2H, m), 2.50-2.37 (8H, br m), 0.96 (6H, s). LCMS (ES$^+$) RT 2.39 minutes, 527 (M+H)$^+$.

EXAMPLE 57

2-[(2-Fluoro-4-iodophenyl)amino]-N-[3-(morpholin-4-yl)propyl]thieno[2,3-b]pyridine-3-carboxamide Prepared from Example 1 (250 mg, 0.56 mmol) and 4-(3-aminopropyl)morpholine (323 mg, 2.24 mmol) by the method of Example 5. After chromatography (5% methanol, 95% dichloromethane) the title compound was obtained as a pale yellow solid (115 mg, 38%). $\delta_H$ (CDCl$_3$) 11.29 (1H, br s), 8.36 (1H, dd, J 1.4, 4.7 Hz), 7.99 (1H, dd, J 1.4, 8.2 Hz), 7.63-7.51 (2H, m), 7.47-7.41 (1H, m), 7.33-7.29 (1H, m), 7.12 (1H, br s), 3.70-3.64 (2H, m), 3.60-3.56 (4H, m), 2.58- 2.54 (2H, m), 2.49-2.46 (4H, m), 1.90-1.82 (2H, m). LCMS (ES$^+$) RT 2.34 minutes, 541 (M+H)$^+$.

EXAMPLE 58

N-(2-Fluoro-4-iodophenyl)-3-(piperazin-1-ylcarbonyl)thieno[2,3-b]pyridin-2-amine piperazine (3.90 g, 45.2 mmol) was dissolved in dry toluene (100 mL) under nitrogen. The mixture was placed in a water bath at 20° C. and trimethylaluminium (2.0M in toluene, 22.6 mL, 45.2 mmol) added slowly. After 10 minutes, Example 1 (4.00 g, 0.56 mmol) was added. The mixture was heated to 100° C. under nitrogen for 6 hours. After cooling to room temperature, the mixture was poured onto a slurry of silica (100 g) in chloroform (400 mL) and methanol (200 mL). After agitation for 10 minutes, the mixture was allowed to stand overnight. Filtration, and concentration of the organic solvent in vacuo, gave crude material, which was purified by triturating with diethyl ether (50 mL), filtering and washing with diethyl ether (20 mL). The title compound was isolated as a yellow solid (3.56 g, 82%), which could be used for further chemistry. The dihydrochloride salt of the title compound was prepared by dissolving the free base (1.60 g, 3.32 mmol) in dichloromethane (30 mL) and methanol (5 mL). HCl in ether (2.0M, 3.34 mL, 6.70 mmol) was added and the mixture concentrated in vacuo. Trituration with diethyl ether (40 mL) and filtration gave the dihydrochloride salt of the title compound (1.80 g, 98%). $\delta_H$ (DMSO-d$_6$) 9.75 (0.25H, br s), 9.43 (1.75H, br s), 9.30 (1H, s), 8.36 (1H, dd, J 1.6, 4.7 Hz), 7.87 (1H, dd, J 1.6, 8.1 Hz), 7.72 (1H, dd, J 1.9, 10.6 Hz), 7.53 (1H, m), 7.39 (1H, dd, J 4.7, 8.1 Hz), 7.22 (1H, dd, J 8.5, 8.5 Hz), 3.75-3.58 (4H, m), 3.17-3.06 (4H, m). LCMS (ES$^+$) RT 2.19 minutes, 483 (M+H)$^+$.

EXAMPLE 59

Ethyl [4-({2-[(2-fluoro-4-iodophenyl)amino]thieno[2,3-b]pyridin-3-yl}carbonyl)-piperazin-1-yl]acetate Example 58 (300 mg, 0.62 mmol) was dissolved in dichloromethane (10 mL) and triethylamine (94 μL, 0.65 mmol) and ethyl chloroacetate (56 μL, 0.65 mmol) added. The mixture was heated to reflux for 12 hours. After cooling and partitioning between dichloromethane and water (25 mL each), the organic layer was dried (Na$_2$SO$_4$) and concentrated in vacuo. Purification by chromatography (silica, 3% methanol, 97% dichloromethane) gave the product as an oil, which was dissolved in diethyl ether (5 mL) and concentrated under high vacuum to give the title compound as a white solid (240 mg, 68%). $\delta_H$ (CDCl$_3$) 9.11 (1H, br s), 8.37 (1H, dd, J 1.5, 4.7 Hz), 7.71 (1H, dd, J 1.5, 8.1 Hz), 7.53-7.49 (2H, m), 7.40 (1H, dd, J 8.4, 8.4 Hz), 7.32-7.28 (1H, m), 4.21 (2H, q, J=7.1 Hz), 3.75-3.61 (4H, m), 3.31 (2H, s), 2.79-2.62 (4H, m), 1.29 (3H, t, J=7.1 Hz). LCMS (ES$^+$) RT 3.26 minutes, 569 (M+H)$^+$.

EXAMPLE 60

[4-({2-[(2-Fluoro-4-iodophenyl)amino]thieno[2,3-b]pyridin-3-yl}carbonyl)piperazin-1-yl]acetic acid Example 59 (213 mg, 0.375 mmol) was dissolved in ethanol (7 mL) and water (7 mL). Sodium hydroxide (15.0 mg, 0.375 mmol) was added and the mixture stirred at room temperature for 18 hours. Freeze-drying gave the title compound as its sodium salt (200 mg, 99%). $\delta_H$ (DMSO-d$_6$) 9.29 (1H, br s), 8.22-8.17 (1H, br m), 7.68 (1H, br d, J=8.0 Hz), 7.56 (1H, br d, J=10.4 Hz), 7.40 (1H, br d, J=8.6 Hz), 7.28-7.20 (1H, br m), 7.07 (1H, dd, J 8.6, 8.6 Hz), 3.42-3.38 (4H, m), 2.65 (2H, s), 2.37-2.35 (4H, m). LCMS (ES$^+$) RT 2.64 minutes, 541 (M+H)$^+$.

EXAMPLE 61 tert-Butyl (3R)-3-[({2-[(2-fluoro-4-iodophenyl) amino]thieno[2,3-b]pyridin-3-yl}-carbonyl)amino] pyrrolidine-1-carboxylate Prepared from Example 1 (250 mg, 0.56 mmol) and (R)-3-amino-1-tert-butoxycarbonylpyrrolidine (417 mg, 2.24 mmol) by the method of Example 5. After chromatography (25% ethyl acetate, 75% dichloromethane) the title compound was obtained as an off-white solid (45 mg, 13%). $\delta_H$ (DMSO-d$_6$) 10.27 (1H, br s), 8.35 (1H, dd, J 1.4, 4.7 Hz), 8.23 (1H, br d, J=6.5 Hz), 8.06 (1H, dd, J 1.4, 8.2 Hz), 7.74 (1H, dd, J 1.9, 10.5 Hz), 7.57 (1H, d, J=8.5 Hz), 7.43 (1H, dd, J 4.7, 8.2 Hz), 7.36 (1H, dd, J 8.6, 8.6 Hz), 4.46-4.40 (1H, br m), 3.57-3.54 (1H, m), 3.52-3.30 (3H, m), 2.15-2.05 (1H, br m), 1.95-1.85 (1H, br m), 1.41 (9H, s). LCMS (ES$^+$) RT 3.70 minutes, 583 (M+H)$^+$.

EXAMPLE 62 tert-Butyl (3S)-3-[({2-[(2-fluoro-4-iodophenyl) amino]thieno[2,3-b]pyridin-3-yl}-carbonyl)amino] pyrrolidine-1-carboxylate Prepared from Example 1 (250 mg, 0.56 mmol) and (S)-3-amino-1-tert-butoxycarbonylpyrrolidine (417 mg, 2.24 mmol) by the method of Example 5. After chromatography (25% ethyl acetate, 75% dichloromethane) the title compound was obtained as an off-white solid (190 mg, 58%). $\delta_H$ (DMSO-d$_6$) 10.27 (1H, br s), 8.35 (1H, dd, J 1.4, 4.7 Hz), 8.23 (1H, br d, J=6.5 Hz), 8.06 (1H, dd, J 1.4, 8.2 Hz), 7.74 (1H, dd, J 1.9, 10.5 Hz), 7.57 (1H, d, J=8.5 Hz), 7.43 (1H, dd, J 4.7, 8.2 Hz), 7.36 (1H, dd, J 8.6, 8.6 Hz), 4.46-4.40 (1H, br m), 3.57-3.54 (1H, m), 3.52-3.30 (3H, m), 2.15-2.05 (1H, br m), 1.95-1.85 (1H, br m), 1.41 (9H, s). LCMS (ES$^+$) RT 3.70 minutes, 583 (M+H)$^+$.

EXAMPLE 63

2-[(2-Fluoro-4-iodophenyl)amino]-N-[(3R)-pyrrolidin-3-yl]thieno[2,3-b]pyridine-3-carboxamide Example 61 (40 mg, 0.069 mmol) was dissolved in dichloromethane (3 mL) and HCl in dioxane (4.0M, 1.0 mL, 4.0 mmol) was added. The mixture was stirred at room temperature for 18 hours. The resultant solid was filtered off and dried under vacuum at 40° C. to give the dihydrochloride salt of the title compound (28 mg, 73%). $\delta_H$ (DMSO-d$_6$) 10.44 (1H, br s), 9.25 (2H, br m), 8.37-8.31 (2H, m), 8.21 (1H, dd, J 1.3, 8.2 Hz), 7.76 (1H, dd, J 1.8, 10.4 Hz), 7.61 (1H, d, J=8.5 Hz), 7.45-7.39 (2H, m), 4.61-4.57 (1H, m), 3.45-3.23 (4H, m), 2.27-2.15 (1H, m), 2.09-1.98 (1H, m). LCMS (ES$^+$) RT 2.30 minutes, 483 (M+H)$^+$.

EXAMPLE 64

2-[(2-Fluoro-4-iodophenyl)amino]-N-[(3S)-pyrrolidin-3-yl]thieno[2,3-b]pyridine-3-carboxamide Example 62 (170 mg, 0.069 mmol) was dissolved in dichloromethane (4 ml) and HCl in dioxane (4.0M, 4.0 ml, 16.0 mmol) was added. The mixture was stirred at room temperature for 18 hours. The resultant solid was filtered off and dried under vacuum at 40° C. to give the dihydrochloride salt of the title compound (150 mg, 92%). $\delta_H$ (DMSO-d$_6$) 10.44 (1H, br s), 9.25 (2H, br m), 8.37-8.31 (2H, m), 8.21 (1H, dd, J 1.3, 8.2 Hz), 7.76 (1H, dd, J 1.8, 10.4 Hz), 7.61 (1H, d, J=8.5 Hz), 7.45-7.39 (2H, m), 4.61-4.57 (1H, m), 3.45-3.23 (4H, m), 2.27-2.15 (1H, m), 2.09-1.98 (1H, m). LCMS (ES$^+$) RT 2.30 minutes, 483 (M+H)$^+$.

EXAMPLE 65

2-[(2-Fluoro-4-iodophenyl)amino]-N-(1-methylpiperidin-4-yl)thieno[2,3-b]pyridine-3-carboxamide Prepared from Example 1 (250 mg, 0.56 mmol) and 4-amino-1-methylpiperidine (255 mg, 2.24 mmol) by the method of Example 5. After chromatography (10% methanol, 90% dichloromethane) the crude material was dissolved in dichloromethane (2 mL) and 2.0M HCl in diethyl ether (2 mL) was added. The resultant solid was filtered off to give the dihydrochloride salt of the title compound as a yellow solid (145 mg, 44%). $\delta_H$ (DMSO-d$_6$) 10.62 (1H, br s), 10.37 (0.8H, s), 10.26 (0.2H, s), 8.40-8.36 (1H, m), 8.31-8.28 (0.8H, m), 8.22-8.20 (0.2H, m), 8.19-8.16 (0.2H, m), 8.10-8.07 (0.8H, m), 7.75-7.71 (1H, m), 7.59-7.56 (1H, m), 7.47-7.31 (2H, m), 4.05 (1H, br m), 3.45-3.05 (5H, m), 2.70 (3H, d, J=6.0 Hz), 2.03-1.85 (4H, m). LCMS (ES$^+$) RT 2.34 minutes, 511 (M+H)$^+$.

EXAMPLE 66

{2-[(2-Fluoro-4-iodophenyl)amino]thieno[2,3-b] pyridin-3-yl}-[(2R)-2-(methoxymethyl)-pyrrolidin-1-yl]-methanone From Intermediate 14 (285 mg, 0.66 mmol), 2M trimethylaluminium in hexane (1.6 mL, 3.30 mmol) and (R)-2-(methoxymethyl)pyrrolidine (383 mg, 3.30 mmol) by the method of Example 5, to give the title compound (17 mg). $\delta_H$ (DMSO-d$_6$) 9.17 (1H, br s), 8.37 (1H, dd, J 4.6, 1.3 Hz), 7.78 (1H, d, J=7.7 Hz), 7.76 (1H, dd, J 10.6, 1.8 Hz), 7.46 (1H, d, J=8.5 Hz), 7.37 (1H, d, J 8.0, 4.6 Hz), 7.05 (1H, t, J=8.5 Hz), 4.10-4.00 (1H, br m), 3.33-3.01 (7H, br m), 1.90-1.64 (4H, br m). LCMS (ES$^+$) RT 3.27 minutes, 215 (M+H)$^+$.

EXAMPLE 67

2-[(2-Fluoro-4-iodophenyl)amino]thieno[2,3-b]pyridine-3-carboxylic acid (cyclopropylmethyl)amide From Intermediate 14 (450 mg, 1.05 mmol), 2M trimethylaluminium in hexane (2.6 mL, 5.26 mmol) and (aminomethyl)cyclopropane (374 mg, 5.26 mmol) by the method of Example 5, to give the title compound (250 mg). $\delta_H$ (DMSO-d$_6$) 10.68 (1H, br s), 8.36 (1H, d, J=3.8 Hz), 8.17 (1H, d, J=8.1 Hz), 8.15-8.00 (1H, br m), 7.75 (1H, d, J=10.4 Hz), 7.60 (1H, d, J=7.6 Hz), 7.47-7.38 (2H, br m), 3.18 (2H, t, J=6.2 Hz), 1.10-1.03 (1H, br m), 0.47-0.41 (2H, br m), 0.28-0.23 (2H, br m). LCMS (ES$^+$) RT 3.54 minutes, 468 (M+H)$^+$.

EXAMPLE 68

2-[(2-Fluoro-4-iodophenyl)amino]-7-oxythieno[2,3-b]pyridine-3-carboxylic acid (N-methoxy-N-methyl) amide To a solution of Intermediate 16 (260 mg, 1.12 mmol) in DMSO was added sodium hydride (50 mg, 1.23 mmol), and the reaction stirred for 10 minutes. Intermediate 1 (328 mg, 1.18 mmol) was added and the reaction stirred for a further 1 h at ambient temperature. The reaction was poured onto water and extracted into ethyl acetate. The organic phase was washed with brine, dried (magnesium sulphate) and concentrated in vacuo. The crude product was purified by chromatography (SiO$_2$, 10% methanol in ethyl acetate) yielding the required product as a pale yellow solid (64 mg). $\delta_H$ (DMSO-d$_6$) 9.41 (1H, s), 8.20 (1H, dd, J 5.9, 1.0 Hz), 7.74 (1H, dd, J 10.3, 1.9 Hz), 7.57-7.54 (1H, m), 7.48-7.38 (2H, m), 7.22 (1H, t, J=8.6 Hz), 3.47 (3H, s), 3.17 (3H, s). LCMS (ES$^+$) RT 2.70 minutes, 474 (M+H)$^+$.

EXAMPLE 69

2-[(2-Fluoro-4-iodophenyl)amino]thieno[2,3-b]pyridine-3-carboxylic acid (N-methoxy-N-methyl)amide Example 68 (64 mg, 0.13 mmol) and triphenyl phosphine (177 mg, 0.68 mmol) in THF (1 mL) were heated at 65° C. overnight. Phosphorus trichloride (34 mg, 0.39 mmol) was added and the reaction stirred at ambient temperature for 90 minutes. The reaction was quenched with sodium hydrogen carbonate solution and the product extracted into DCM, dried (magnesium sulphate) and concentrated in vacuo. After preparative HPLC, the required product (10 mg) was obtained as an off-white solid. $\delta_H$ (DMSO-d$_6$) 9.23 (1H, s), 8.35 (1H, dd, J 4.7, 1.6 Hz), 7.84 (1H, dd, J 8.1, 1.6 Hz), 7.70 (1H, dd, J 10.3, 1.9 Hz), 7.53 (1H, d, J=8.4 Hz), 7.37 (1H, dd, J 8.1, 4.7 Hz), 7.22 (1H, t, J=8.6 Hz), 3.47 (3H, s), 3.20 (3H, s). LCMS (ES$^+$) RT 3.23 minutes, 458 (M+H)$^+$.

EXAMPLE 70

{2-[(2-Fluoro-4-iodophenyl)amino]thieno[2,3-b]pyridin-3-yl}-[(2R)-2-(hydroxymethyl)-piperazin-1-yl]-methanone A solution of Example 51 (80 mg, 0.13 mmol) in methanol (2 mL) was treated with 4M HCl in 1,4-dioxane (5 mL) and stirred at r.t. for 3 h. The reaction mixture was concentrated in vacuo to give a yellow gum, which was dissolved in methanol (20 mL) and water (5 mL), then basified to pH 11 with 25% aq. ammonium hydroxide. The aqueous solution was extracted with DCM (3×25 mL), and the organic extracts were combined, dried (Na$_2$SO$_4$), filtered and concentrated in vacuo. The crude product was subjected to column chromatography (SiO$_2$, 95:4:1 DCM/methanol/25% aq. ammonium hydroxide) to give the title compound as a mixture of 2 rotamers, which were freeze-dried overnight from acetonitrile/water to give a cream-coloured powder (63 mg, 94%). $\delta_H$ (DMSO-d$_6$, 120° C., contains rotamers) 8.37-8.36 (1H, m), 8.29-8.28 (0.44H, m), 8.33 (0.56H, dd, J 1.4, 8.0 Hz), 7.75 (0.44H, dd, J 1.8, 10.0 Hz), 7.68-7.66 (0.44H, m), 7.58 (0.56H, dd, J 1.9, 10.5 Hz), 7.48-7.44 (1H, m), 7.39-7.33 (1H, m), 7.17-7.13 (0.56H, m), 4.31-4.29 (1H, m), 4.00 (1H, m), 3.74-3.60 (2H, m), 3.10-2.83 (3H, m), 2.76-2.65 (2H, m), 2.60-2.53 (1H, m). LCMS RT 2.07 and 1.95 minutes, (ES$^+$) 513 (M+H)$^+$.

When ranges are used herein, for example, for biological activity, such as binding data, chemical properties, such as chemical formulae, or dosage ranges, all combinations and subcombinations of ranges and specific embodiments therein are intended to be included.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A method for the treatment of a disorder for which the administration of a selective MEK inhibitor is indicated which comprises administering to a patient in need of such treatment an effective amount of a compound or a pharmaceutically acceptable salt, or N-oxide thereof of Formula I:

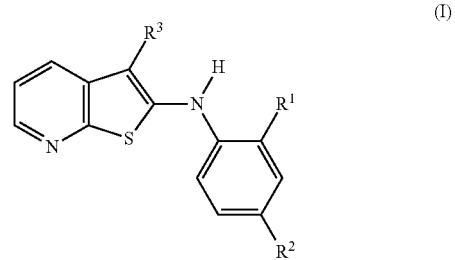

(I)

wherein
   $R^1$ is hydrogen, halogen or $C_{1-6}$ alkyl;
   $R^2$ is halogen or $C_{1-6}$ alkyl;
   $R^3$ is hydrogen, cyano, —CO$_2$R$^a$, —CONR$^b$R$^c$ or —CON(OR$^b$)R$^c$;
   $R^a$ is $C_{1-6}$ alkyl;
   $R^b$ is hydrogen, optionally substituted $C_{1-6}$ alkyl, optionally substituted $C_{3-7}$ cycloalkyl, optionally substituted $C_{3-7}$ cycloalkyl($C_{1-6}$)alkyl, optionally substituted aryl, optionally substituted aryl($C_{1-6}$)alkyl, optionally substituted $C_{3-7}$ heterocycloalkyl, optionally substituted $C_{3-7}$ heterocycloalkyl($C_{1-6}$)alkyl, optionally substituted heteroaryl or optionally substituted heteroaryl($C_{1-6}$)alkyl;
   $R^c$ is hydrogen or $C_{1-6}$ alkyl optionally substituted with one or more hydroxyl groups; or $R^b$ and $R^c$ are taken together with the nitrogen atom to which they are attached to form a cyclic group selected from optionally substituted azetidinyl, optionally substituted pyrrolidinyl, optionally substituted piperidinyl, optionally substituted morpholinyl, optionally substituted thiomorpholinyl, optionally substituted piperazinyl, optionally substituted homopiperidinyl, optionally substituted homomorpholinyl and optionally substituted homopiperazinyl.

2. A method according to claim 1 wherein the disorder is selected from the group consisting of an autoimmune or inflammatory disorder, a cardiovascular disorder, a proliferative disorder, an oncological disorder, and pain or a nociceptive disorder.

3. A method according to claim 2 wherein the disorder is an autoimmune or inflammatory disorder.

4. A method according to claim 2 wherein the disorder is a cardiovascular disorder.

5. A method according to claim 2 wherein the disorder is a proliferative disorder.

6. A method according to claim 5 wherein the proliferative disorder is restenosis.

7. A method according to claim 2 wherein the disorder is an oncological disorder.

8. A method according to claim 7 wherein the oncological disorder is selected from the group consisting of leukemia, glioblastoma, lymphoma, melanoma, and human cancers of the liver, bone, skin, brain, pancreas, lung, breast, stomach, colon, rectum, prostate, ovary and cervix.

9. A method according to claim 2 wherein the disorder is pain or a nociceptive disorder.

10. A method according to claim 1 wherein the compound of Formula I is selected from the group consisting of:

Ethyl 2-[(2-fluoro-4-iodophenyl)amino]thieno[2,3-b]pyridine-3-carboxylate;
2-[(2-Fluoro-4-iodophenyl)amino]-N-methylthieno[2,3-b]pyridine-3-carboxamide;
2-[(2-Fluoro-4-iodophenyl)amino]-N,N-dimethylthieno[2,3-b]pyridine-3-carboxamide;
N-(2-Fluoro-4-iodophenyl)-3-(morpholin-4-ylcarbonyl)thieno[2,3-b]pyridin-2-amine;
N-(2-Fluoro-4-iodophenyl)-3-[(4-methylpiperazin-1-yl)carbonyl]thieno[2,3-b]-pyridin-2-amine;
2-[(4-Bromo-2-fluorophenyl)amino]-N-(2,3-dihydroxypropyl)thieno[2,3-b]-pyridine-3-carboxamide;
2-[(2-Fluoro-4-iodophenyl)amino]-N-(2,3-dihydroxypropyl)thieno[2,3-b]pyridine-3-carboxamide;
Ethyl 2-[(2-fluoro-4-iodophenyl)amino]thieno[2,3-b]pyridine-3-carboxylate 7-oxide;
N-(2,3-Dihydroxypropyl)-2-[(2-fluoro-4-iodophenyl)amino]thieno[2,3-b]pyridine-3-carboxamide 7-oxide;
2-[(2-Fluoro-4-iodophenyl)amino]thieno[2,3-b]pyridine-3-carbonitrile;
2-[(2-Fluoro-4-iodophenyl)amino]thieno[2,3-b]pyridine-3-carboxylic acid amide;
[2-[(2-Fluoro-4-iodophenyl)amino]thieno[2,3-b]pyridin-3-yl](pyrrolidin-1-yl)methanone;
2-[(2-Fluoro-4-iodophenyl)amino]thieno[2,3-b]pyridine-3-carboxylic acid (3-hydroxypropyl)amide;
2-[(2-Fluoro-4-iodophenyl)amino]thieno[2,3-b]pyridine-3-carboxylic acid (2(S),3-dihydroxypropyl)amide;
2-[(2-Fluoro-4-iodophenyl)amino]thieno[2,3-b]pyridine-3-carboxylic acid (2(R),3-dihydroxypropyl)amide;
2-[(4-Bromo-2-fluorophenyl)amino]thieno[2,3-b]pyridine-3-carboxylic acid methylamide;
2-[(4-Iodophenyl)amino]thieno[2,3-b]pyridine-3-carboxylic acid ethyl ester;
2-[(4-Iodo-2-methylphenyl)amino]thieno[2,3-b]pyridine-3-carbonitrile;
2-[(4-Bromo-2-fluorophenyl)amino]thieno[2,3-b]pyridine-3-carbonitrile;
2-[(2-Chloro-4-iodophenyl)amino]thieno[2,3-b]pyridine-3-carbonitrile;
2-[(2-Fluoro-4-iodophenyl)amino]thieno[2,3-b]pyridine-3-carboxylic acid (2-amino-2-methylpropyl)amide;
2-[(2-Fluoro-4-iodophenyl)amino]thieno[2,3-b]pyridine-3-carboxylic acid [(4R)-2,2-dimethyl-[1,3]dioxolan-4-ylmethoxy]amide;
2-[(2-Fluoro-4-iodophenyl)amino]thieno[2,3-b]pyridine-3-carboxylic acid [(2R)-2,3-dihydroxypropoxy]amide;
(1-{2-[(2-Fluoro-4-iodophenyl)amino]thieno[2,3-b]pyridine-3-carbonyl}piperidin-4-yl)-carbamic acid tert-butyl ester;
2-[(2-Fluoro-4-iodophenyl)amino]thieno[2,3-b]pyridine-3-carboxylic acid (4-aminopiperidin-1-yl)amide dihydrochloride;
2-[(2-Fluoro-4-iodophenyl)amino]thieno[2,3-b]pyridine-3-carboxylic acid (2-hydroxy-1-methylethyl)amide;
3-[({2-[(2-Fluoro-4-iodophenyl)amino]thieno[2,3-b]pyridine-3-carbonyl}amino)-methyl]azetidine-1-carboxylic acid tert-butyl ester;
(1-{2-[(2-Fluoro-4-iodophenyl)amino]thieno[2,3-b]pyridine-3-carbonyl}azetidin-3-ylmethyl)carbamic acid tert-butyl ester;
3-({2-[(2-Fluoro-4-iodophenyl)amino]thieno[2,3-b]pyridine-3-carbonyl}amino)-azetidine-1-carboxylic acid tert-butyl ester;
[3-(Aminomethyl)azetidin-1-yl]-{2-[(2-fluoro-4-iodophenyl)amino]thieno[2,3-b]pyridin-3-yl}methanone;
2-[(2-Fluoro-4-iodophenyl)amino]thieno[2,3-b]pyridine-3-carboxylic acid [(2R)-pyrrolidin-2-ylmethyl]amide;
2-[(2-Fluoro-4-iodophenyl)amino]thieno[2,3-b]pyridine-3-carboxylic acid [(2S)-pyrrolidin-2-ylmethyl]amide;
(3S)-({2-[(2-Fluoro-4-iodophenyl)amino]thieno[2,3-b]pyridine-3-carbonyl}-amino)-piperidine-1-carboxylic acid tert-butyl ester;
(3R)-({2-[(2-Fluoro-4-iodophenyl)amino]thieno[2,3-b]pyridine-3-carbonyl}-amino)piperidine-1-carboxylic acid tert-butyl ester;
2-[(2-Fluoro-4-iodophenyl)amino]thieno[2,3-b]pyridine-3-carboxylic acid [(3S)-piperidin-3-yl]amide dihydrochloride;
2-[(2-Fluoro-4-iodophenyl)amino]thieno[2,3-b]pyridine-3-carboxylic acid [(3R)-piperidin-3-yl]amide dihydrochloride;
(1-{2-[(2-Fluoro-4-iodophenyl)amino]thieno[2,3-b]pyridine-3-carbonyl}-(3R)-pyrrolidin-3-yl)carbamic acid tert-butyl ester;
(1-{2-[(2-Fluoro-4-iodophenyl)amino]thieno[2,3-b]pyridine-3-carbonyl}-(3S)-pyrrolidin-3-yl)carbamic acid tert-butyl ester;
(1-{2-[(2-Fluoro-4-iodophenyl)amino]thieno[2,3-b]pyridine-3-carbonyl}azetidin-3-yl)-carbamic acid tert-butyl ester;
4-({2-[(2-Fluoro-4-iodophenyl)amino]thieno[2,3-b]pyridine-3-carbonyl}amino)-piperidine-1-carboxylic acid tert-butyl ester;
[(3R)-3-Aminopyrrolidin-1-yl]-{2-[(2-fluoro-4-iodophenyl)amino]thieno[2,3-b]-pyridin-3-yl}methanone;
[(3S)-3-Aminopyrrolidin-1-yl]-{2-[(2-fluoro-4-iodophenyl)amino]thieno[2,3-b]-pyridin-3-yl}methanone;
2-[(2-Fluoro-4-iodophenyl)amino]thieno[2,3-b]pyridine-3-carboxylic acid (piperidin-4-yl)amide;
(3-Aminoazetidin-1-yl)-{2-[(2-fluoro-4-iodophenyl)amino]thieno[2,3-b]pyridin-3-yl]methanone;
2-[(2-Fluoro-4-iodophenyl)amino]thieno[2,3-b]pyridine-3-carboxylic acid bis (2-hydroxyethyl)amide;
{2-[(2-Fluoro-4-iodophenyl)amino]thieno[2,3-b]pyridin-3-yl}-(3-hydroxy-azetidin-1-yl)-methanone;
{2-[(2-Fluoro-4-iodophenyl)amino]thieno[2,3-b]pyridin-3-yl}-[(3R)-3-hydroxy-pyrrolidin-1-yl]-methanone;
{2-[(2-Fluoro-4-iodophenyl)amino]thieno[2,3-b]pyridin-3-yl}-[(3S)-3-hydroxy-pyrrolidin-1-yl]-methanone;
{2-[(2-Fluoro-4-iodophenyl)amino]thieno[2,3-b]pyridin-3-yl}-[2-(hydroxyl-methyl)piperidin-1-yl]-methanone;
{2-[(2-Fluoro-4-iodophenyl)amino]thieno[2,3-b]pyridin-3-yl}-[(3S)-3-(hydroxyl-methyl)-morpholin-4-yl]-methanone;
4-{2-[(2-Fluoro-4-iodophenyl)amino]thieno[2,3-b]pyridine-3-carbonyl}-(3R)-3-(hydroxymethyl)piperazine-1-carboxylic acid tert-butyl ester;
2-[(2-Fluoro-4-iodophenyl)amino]thieno[2,3-b]pyridine-7-oxide;
2-[(2-Fluoro-4-iodophenyl)amino]-N-[2-(morpholin-4-yl)ethyl]thieno[2,3-b]-pyridine-3-carboxamide;
2-[4-({2-[(2-Fluoro-4-iodophenyl)amino]thieno[2,3-b]pyridin-3-yl}carbonyl)-piperazin-1-yl]ethanol;

3-(1,4-Diazepan-1-ylcarbonyl)-N-(2-fluoro-4-iodophenyl)thieno[2,3-b]pyridin-2-amine;
N-[3-(Dimethylamino)-2,2-dimethylpropyl]-2-[(2-fluoro-4-iodophenyl)amino]-thieno[2,3-b]pyridine-3-carboxamide;
2-[(2-Fluoro-4-iodophenyl)amino]-N-[3-(morpholin-4-yl)propyl]thieno[2,3-b]-pyridine-3-carboxamide;
N-(2-Fluoro-4-iodophenyl)-3-(piperazin-1-ylcarbonyl)thieno[2,3-b]pyridin-2-amine;
Ethyl [4-({2-[(2-fluoro-4-iodophenyl)amino]thieno[2,3-b]pyridin-3-yl}carbonyl)-piperazin-1-yl]acetate;
[4-({2-[(2-Fluoro-4-iodophenyl)amino]thieno[2,3-b]pyridin-3-yl}carbonyl)-piperazin-1-yl]acetic acid;
tert-Butyl (3R)-3-[({2-[(2-fluoro-4-iodophenyl)amino]thieno[2,3-b]pyridin-3-yl}-carbonyl)amino]pyrrolidine-1-carboxylate;
tert-Butyl (3S)-3-[({2-[(2-fluoro-4-iodophenyl)amino]thieno[2,3-b]pyridin-3-yl}-carbonyl)amino]pyrrolidine-1-carboxylate;
2-[(2-Fluoro-4-iodophenyl)amino]-N-[(3R)-pyrrolidin-3-yl]thieno[2,3-b]pyridine-3-carboxamide;
2-[(2-Fluoro-4-iodophenyl)amino]-N-[(3S)-pyrrolidin-3-yl]thieno[2,3-b]pyridine-3-carboxamide;
2-[(2-Fluoro-4-iodophenyl)amino]-N-(1-methylpiperidin-4-yl)thieno[2,3-b]-pyridine-3-carboxamide;
{2-[(2-Fluoro-4-iodophenyl)amino]thieno[2,3-b]pyridin-3-yl}-[(2R)-2-(methoxymethyl)-pyrrolidin-1-yl]-methanone;
2-[(2-Fluoro-4-iodophenyl)amino]thieno[2,3-b]pyridine-3-carboxylic acid (cyclopropylmethyl)amide;
2-[(2-Fluoro-4-iodophenyl)amino]-7-oxythieno[2,3-b]pyridine-3-carboxylic acid (N-methoxy-N-methyl)amide;
2-[(2-Fluoro-4-iodophenyl)amino]thieno[2,3-b]pyridine-3-carboxylic acid (N-methoxy-N-methyl)amide; and
{2-[(2-Fluoro-4-iodophenyl)amino]thieno[2,3-b]pyridin-3-yl}-[(2R)-2-(hydroxymethyl)-piperazin-1-yl]-methanone; and
pharmaceutically acceptable salts or N-oxides thereof.

11. A method for the treatment of a disorder for which the administration of a selective MEK inhibitor is indicated which comprises administering to a patient in need of such treatment an effective amount of a compound or a pharmaceutically acceptable salt, or N-oxide thereof of Formula I:

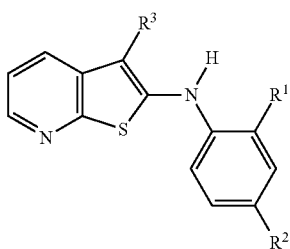

(I)

wherein
R$^1$ is hydrogen, halogen or C$_{1-6}$ alkyl;
R$^2$ is halogen or C$_{1-6}$ alkyl;
R$^3$ is —CONR$^b$R$^c$; and
R$^b$ and R$^c$ are taken together with the nitrogen atom to which they are attached to form a cyclic group selected from optionally substituted azetidin-1-yl, optionally substituted pyrrolidin-1-yl, optionally substituted piperidin-1-yl, optionally substituted morpholin-4-yl, optionally substituted thiomorpholin-4-yl, optionally substituted piperazin-1-yl, optionally substituted homopiperidin-1-yl, optionally substituted homomorpholin-4-yl and optionally substituted homopiperazin-1-yl;
wherein said cyclic group formed when R$^b$ and R$^c$ are taken together with the nitrogen atom to which they are attached is optionally substituted with: C$_{1-6}$ alkyl, C$_{1-6}$ alkoxy, hydroxy, hydroxy(C$_{1-6}$)alkyl, amino (C$_{1-6}$)alkyl, (amino)(hydroxy)-(C$_{1-6}$)alkyl, halogen, oxo, C$_{2-6}$ alkylcarbonyl, carboxy, C$_{2-6}$ alkoxycarbonyl, di(C$_{1-6}$)alkylhydrazinylcarbonyl, amino, C$_{1-6}$ alkylamino, di(C$_{1-6}$)alkylamino, C$_{2-6}$ alkylcarbonylamino, aminocarbonylamino, aminocarbonyl, C$_{1-6}$ alkylaminocarbonyl, di(C$_{1-6}$)alkylaminocarbonyl, aminosulfonyl, C$_{1-6}$ alkylsulfonyl, C$_{1-6}$ alkylaminocarbonyl(C$_{1-6}$)alkyl, C$_{1-6}$ alkoxy(C$_{1-6}$)alkyl, carboxy(C$_{1-6}$)alkyl, C$_{2-6}$ alkoxycarbonyl(C$_{1-6}$)alkyl, C$_{2-6}$ alkoxycarbonylamino or C$_{2-6}$ alkoxycarbonylamino(C$_{1-6}$)alkyl.

12. A method according to claim 11 wherein the disorder is selected from the group consisting of an autoimmune or inflammatory disorder, a cardiovascular disorder, a proliferative disorder, an oncological disorder, and pain or a nociceptive disorder.

13. A method according to claim 12 wherein the disorder is an autoimmune or inflammatory disorder.

14. A method according to claim 12 wherein the disorder is a cardiovascular disorder.

15. A method according to claim 12 wherein the disorder is a proliferative disorder.

16. A method according to claim 15 wherein the proliferative disorder is restenosis.

17. A method according to claim 12 wherein the disorder is an oncological disorder.

18. A method according to claim 17 wherein the oncological disorder is selected from the group consisting of leukemia, glioblastoma, lymphoma, melanoma, and human cancers of the liver, bone, skin, brain, pancreas, lung, breast, stomach, colon, rectum, prostate, ovary and cervix.

19. A method according to claim 12 wherein the disorder is pain or a nociceptive disorder.

20. A method according to claim 11 wherein the compound of Formula I is selected from the group consisting of:
N-(2-Fluoro-4-iodophenyl)-3-(morpholin-4-ylcarbonyl)thieno[2,3-b]pyridin-2-amine;
N-(2-Fluoro-4-iodophenyl)-3-[(4-methylpiperazin-1-yl)carbonyl]thieno[2,3-b]-pyridin-2-amine;
[2-[(2-Fluoro-4-iodophenyl)amino]thieno[2,3-b]pyridin-3-yl](pyrrolidin-1-yl)methanone;
(1-{2-[(2-Fluoro-4-iodophenyl)amino]thieno[2,3-b]pyridine-3-carbonyl}piperidin-4-yl)-carbamic acid tert-butyl ester;
2-[(2-Fluoro-4-iodophenyl)amino]thieno[2,3-b]pyridine-3-carboxylic acid (4-aminopiperidin-1-yl)amide dihydrochloride;
(1-{2-[(2-Fluoro-4-iodophenyl)amino]thieno[2,3-b]pyridine-3-carbonyl}azetidin-3-ylmethyl)carbamic acid tert-butyl ester;
[3-(Aminomethyl)azetidin-1-yl]-{2-[(2-fluoro-4-iodophenyl)amino]thieno[2,3-b]pyridin-3-yl}methanone;
(1-{2-[(2-Fluoro-4-iodophenyl)amino]thieno[2,3-b]pyridine-3-carbonyl}-(3R)-pyrrolidin-3-yl)carbamic acid tert-butyl ester;

(1-{2-[(2-Fluoro-4-iodophenyl)amino]thieno[2,3-b]pyridine-3-carbonyl}-(3S)-pyrrolidin-3-yl)carbamic acid tert-butyl ester;

(1-{2-[(2-Fluoro-4-iodophenyl)amino]thieno[2,3-b]pyridine-3-carbonyl}azetidin-3-yl)-carbamic acid tert-butyl ester;

[(3R)-3-Aminopyrrolidin-1-yl]-{2-[(2-fluoro-4-iodophenyl)amino]thieno[2,3-b]-pyridin-3-yl}methanone;

[(3S)-3-Aminopyrrolidin-1-yl]-{2-[(2-fluoro-4-iodophenyl)amino]thieno[2,3-b]-pyridin-3-yl}methanone;

(3-Aminoazetidin-1-yl)-{2-[(2-fluoro-4-iodophenyl)amino]thieno[2,3-b]pyridin-3-yl}methanone;

{2-[(2-Fluoro-4-iodophenyl)amino]thieno[2,3-b]pyridin-3-yl}-(3-hydroxy-azetidin-1-yl)-methanone;

{2-[(2-Fluoro-4-iodophenyl)amino]thieno[2,3-b]pyridin-3-yl}-[(3R)-3-hydroxy-pyrrolidin-1-yl]-methanone;

{2-[(2-Fluoro-4-iodophenyl)amino]thieno[2,3-b]pyridin-3-yl}-[(3S)-3-hydroxy-pyrrolidin-1-yl]-methanone;

{2-[(2-Fluoro-4-iodophenyl)amino]thieno[2,3-b]pyridin-3-yl}-[2-(hydroxyl-methyl)piperidin-1-yl]-methanone;

{2-[(2-Fluoro-4-iodophenyl)amino]thieno[2,3-b]pyridin-3-yl}-[(3S)-3-(hydroxyl-methyl)-morpholin-4-yl]-methanone;

4-{2-[(2-Fluoro-4-iodophenyl)amino]thieno[2,3-b]pyridine-3-carbonyl}-(3R)-3-(hydroxymethyl)piperazine-1-carboxylic acid tert-butyl ester;

2-[4-({2-[(2-Fluoro-4-iodophenyl)amino]thieno[2,3-b]pyridin-3-yl}carbonyl)-piperazin-1-yl]ethanol;

3-(1,4-Diazepan-1-ylcarbonyl)-N-(2-fluoro-4-iodophenyl)thieno[2,3-b]pyridin-2-amine;

N-(2-Fluoro-4-iodophenyl)-3-(piperazin-1-ylcarbonyl)thieno[2,3-b]pyridin-2-amine;

Ethyl [4-({2-[(2-fluoro-4-iodophenyl)amino]thieno[2,3-b]pyridin-3-yl}carbonyl)-piperazin-1-yl]acetate;

[4-({2-[(2-Fluoro-4-iodophenyl)amino]thieno[2,3-b]pyridin-3-yl}carbonyl)-piperazin-1-yl]acetic acid;

{2-[(2-Fluoro-4-iodophenyl)amino]thieno[2,3-b]pyridin-3-yl}-[(2R)-2-(methoxymethyl)-pyrrolidin-1-yl]-methanone; and {2-[(2-Fluoro-4-iodophenyl)amino]thieno[2,3-b]pyridin-3-yl}-[(2R)-2-(hydroxymethyl)-piperazin-1-yl]-methanone; and pharmaceutically acceptable salts or N-oxides thereof.

\* \* \* \* \*